(12) United States Patent
Matheny

(10) Patent No.: US 9,060,969 B2
(45) Date of Patent: *Jun. 23, 2015

(54) COMPOSITIONS FOR PREVENTING CARDIAC ARRHYTHMIA

(71) Applicant: CORMATRIX CARDIOVASCULAR, INC., Roswell, GA (US)

(72) Inventor: Robert G Matheny, Norcross, GA (US)

(73) Assignee: CORMATRIX CARDIOVASCULAR, INC., Roswell, GA (US)

( * ) Notice: Subject to any disclaimer, the term of this patent is extended or adjusted under 35 U.S.C. 154(b) by 130 days.

This patent is subject to a terminal disclaimer.

(21) Appl. No.: 13/926,026

(22) Filed: Jun. 25, 2013

(65) Prior Publication Data

US 2013/0316013 A1 Nov. 28, 2013

Related U.S. Application Data

(63) Continuation of application No. 13/480,140, filed on May 24, 2012, now Pat. No. 8,877,224.

(51) Int. Cl.
| | |
|---|---|
| *A61K 35/12* | (2006.01) |
| *A61K 35/36* | (2006.01) |
| *A61K 35/34* | (2006.01) |
| *A61L 27/56* | (2006.01) |
| *A61L 27/00* | (2006.01) |
| *A61L 27/36* | (2006.01) |
| *A61L 27/38* | (2006.01) |
| *A61L 27/54* | (2006.01) |
| *A61L 27/58* | (2006.01) |

(52) U.S. Cl.
CPC ............ *A61K 35/12* (2013.01); *A61L 27/00* (2013.01); *A61L 27/3633* (2013.01); *A61L 27/3683* (2013.01); *A61L 27/3637* (2013.01); *A61K 35/34* (2013.01); *A61K 35/36* (2013.01); *A61L 27/3839* (2013.01); *A61L 27/54* (2013.01); *A61L 27/56* (2013.01); *A61L 27/58* (2013.01); *A61L 2300/236* (2013.01); *A61L 2300/41* (2013.01); *A61L 2300/422* (2013.01); *A61L 2300/64* (2013.01); *A61L 2430/20* (2013.01)

(58) Field of Classification Search
CPC ............ A61L 27/3852; A61L 27/3895; A61L 27/425
USPC .......................................................... 424/423
See application file for complete search history.

(56) References Cited

U.S. PATENT DOCUMENTS

2007/0265699 A1* 11/2007 Grewe et al. ................. 623/1.24

OTHER PUBLICATIONS

Sawada et al. Journal of Chemical Toxicology and Biotechnology, v83, p. 943-949. 2008.*
Isenschmid et al. Journal of Biotechnology, v39, p. 229-237. 1995.*
Zhang et al. Journal of Supercritical Fluids, v38, p. 354-372. 2006.*

* cited by examiner

*Primary Examiner* — Audrea Buckley
(74) *Attorney, Agent, or Firm* — Francis Law Group

(57) ABSTRACT

Disclosed herein are compositions and methods for treating or preventing a cardiac arrhythmia in a subject.

8 Claims, 12 Drawing Sheets

COMPOSITIONS FOR PREVENTING CARDIAC ARRHYTHMIA

CROSS-REFERENCE TO RELATED PATENT APPLICATIONS

This application is a Continuation of U.S. application Ser. No. 13/480,140, filed on May 24, 2012, which is a Continuation-In-Part of U.S. application Ser. No. 12/707,427, filed on Feb. 17, 2010, which claims the benefit of U.S. Provisional Application No. 61/153,402, filed on Feb. 18, 2009; U.S. Provisional Application No. 61/491,723, filed on May 31, 2011; and U.S. Provisional Application No. 61/650,911, filed on May 23, 2012; which are hereby incorporated by reference in their entireties.

BACKGROUND

Cardiac arrhythmias present a significant health problem. Cardiac arrhythmias include, but are not limited to, ventricular tachycardias, supraventricular tachycardias, and atrial fibrillation. Of these, atrial fibrillation is the most common cardiac arrhythmia. It has been estimated that over one million people in the United States alone suffer from atrial fibrillation. The incidence of atrial fibrillation is expected to increase over the next several decades as populations in the United States and Europe trend older because atrial fibrillation tends to become more common with increasing age.

Arrhythmias after cardiac surgery are a major cause of morbidity and mortality. Tolerability of arrhythmia is less in the postoperative period than for similar arrhythmias in the preoperative period. Hemodynamic instability is more likely due to the possibility of myocardial dysfunction. Cardiopulmonary bypass; injury to the conduction system during surgery; and metabolic and electrolyte abnormalities, especially hypokalemia and hypomagnesemia, contribute to the increased incidence of postoperative arrhythmias. Stress of the surgery with enhanced sympathetic tone and use of inotropic support are added factors. Delayed arrhythmia can occur due to scar-related re-entry.

Atrial fibrillation can be treated with medication intended to maintain normal sinus rhythm and/or decrease ventricular response rates. Specifically, many of the past attempts have been confined to pharmacotherapy, radiofrequency ablation, use of implantable devices, and related approaches. While drug therapy remains a popular route for reducing some arrhythmic events, there has been recognition that systemic effects are often poorly tolerated. Moreover, there is belief that proarrhythmic tendencies exhibited by many drugs can increase mortality in many situations. It would be desirable to have more effective compositions and methods for treating or preventing cardiac arrhythmias.

The invention generally relates to sterilized, acellular extracellular matrix compositions and methods of making such compositions for use in treating or preventing cardiac arrhythmias. More particularly, the invention relates to methods of contemporaneously sterilizing and decellularizing extracellular matrix compositions, as well as the sterilized, acellular compositions resulting from such methods for use in subjects who have undergone heart surgery or had a myocardial infarction to treat or prevent cardiac arrhythmia.

Conventional techniques for sterilizing tissue compositions often alter the properties of the tissue compositions and/or damage important components of the tissue compositions, such as growth factors. Consequently, these conventional sterilization techniques often render tissue compositions unfit for their intended purposes. For example, ethylene oxide is a toxic, mutagenic, and carcinogenic substance that can weaken tissue compositions, reduce the growth factor content of tissue compositions, and denature proteins within tissue compositions. Similarly, conventional steam sterilization techniques are incompatible with the biopolymers of tissue compositions, and gamma radiation causes significant decreases in the integrity of tissue compositions. Although there are known techniques for sterilizing tissue compositions without altering the properties of the tissue compositions, many of these techniques, such as anti-bacterial washes, often fail to completely sterilize the tissue compositions and/or leave residual toxic contaminants in the tissue compositions.

Additionally, when tissue compositions are designed for implantation within the body of a subject, the tissue compositions must often be exposed to a separate, time-consuming decellularization process. This decellularization process is intended to remove cells from the tissue compositions, thereby decreasing the likelihood that the subject's immune system will reject the implanted tissue compositions and/or generate a significant inflammatory response. However, conventional decellularization techniques merely decellularize portions of the tissue compositions such that native cells remain in the tissue compositions following the decelluarization process.

U.S. Pat. No. 7,108,832 (the '832 patent), which is assigned to NovaSterilis, Inc., discloses a method that sterilizes various materials through the use of supercritical carbon dioxide. However, as with other known sterilization methods, tissue compositions that are sterilized using the process disclosed in the '832 patent must be exposed to a separate decellularization process, as described above.

Accordingly, there is a need in the art for a method of sterilizing and decellularizing a tissue composition, such as an extracellular matrix composition. More particularly, there is a need in the art for a method of (a) sterilizing a tissue composition while maintaining the native properties of the tissue composition and (b) decellularizing the tissue composition such that the tissue composition is acellular. There is still a further need for a method of enhancing the incorporation of additives into a tissue composition during sterilization and/or decellularization of the tissue composition for purposes of treating or preventing cardiac arrhythmia.

SUMMARY

In accordance with the purpose of this invention, as embodied and broadly described herein, this invention relates to compositions and methods for treating or preventing cardiac arrhythmia in a subject.

This invention also relates to methods of sterilizing and decellularizing an extracellular matrix (ECM) material for use in treating or preventing cardiac arrhythmia in a subject who has undergone heart surgery or had a myocardial infarction. In one aspect, the methods include harvesting of a selected ECM tissue, freezing the selected ECM tissue, thawing the selected ECM tissue, and isolating an ECM material. The isolated ECM material is subjected to incubation and rinsing before it is processed in supercritical carbon dioxide and subsequently exposed to rapid depressurization. During or after the rapid depressurization of the ECM material, one or more additives can be incorporated into the ECM material to impart desired characteristics to the resulting ECM composition. Rapid depressurization enhances the incorporation of the one or more additives into the ECM composition. Sterilized, acellular ECM compositions produced using the disclosed methods are also disclosed.

Additional advantages of the disclosed methods and compositions will be set forth in part in the description which follows and, in part, will be understood from the description, or may be learned by practice of the disclosed methods and compositions. The advantages of the disclosed methods and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

These and other features of the preferred embodiments of the invention will become more apparent in the detailed description in which reference is made to the appended drawings wherein:

FIG. 1 shows the DNA content of each SIS composition following sterilization.

FIG. 2 shows the percentage of DNA that was removed from each SIS composition following sterilization, as compared to raw, unprocessed SIS.

FIG. 3 shows the bFGF content of each SIS composition (normalized by dry weight of samples) following sterilization.

FIG. 4 shows the active TGF-$\beta$ content of each SIS composition (normalized by dry weight of samples) following sterilization.

FIG. 5 shows the bFGF content for each SIS composition (normalized by dry weight of samples) following rapid depressurization.

FIG. 6 shows the tensile strength measured for each SIS composition following sterilization.

FIG. 7 shows the bFGF enzyme-linked immunosorbent assay (ELISA) results for each SIS composition (normalized by dry weight of samples) following sterilization and/or decellularization.

DETAILED DESCRIPTION

Figure 1:
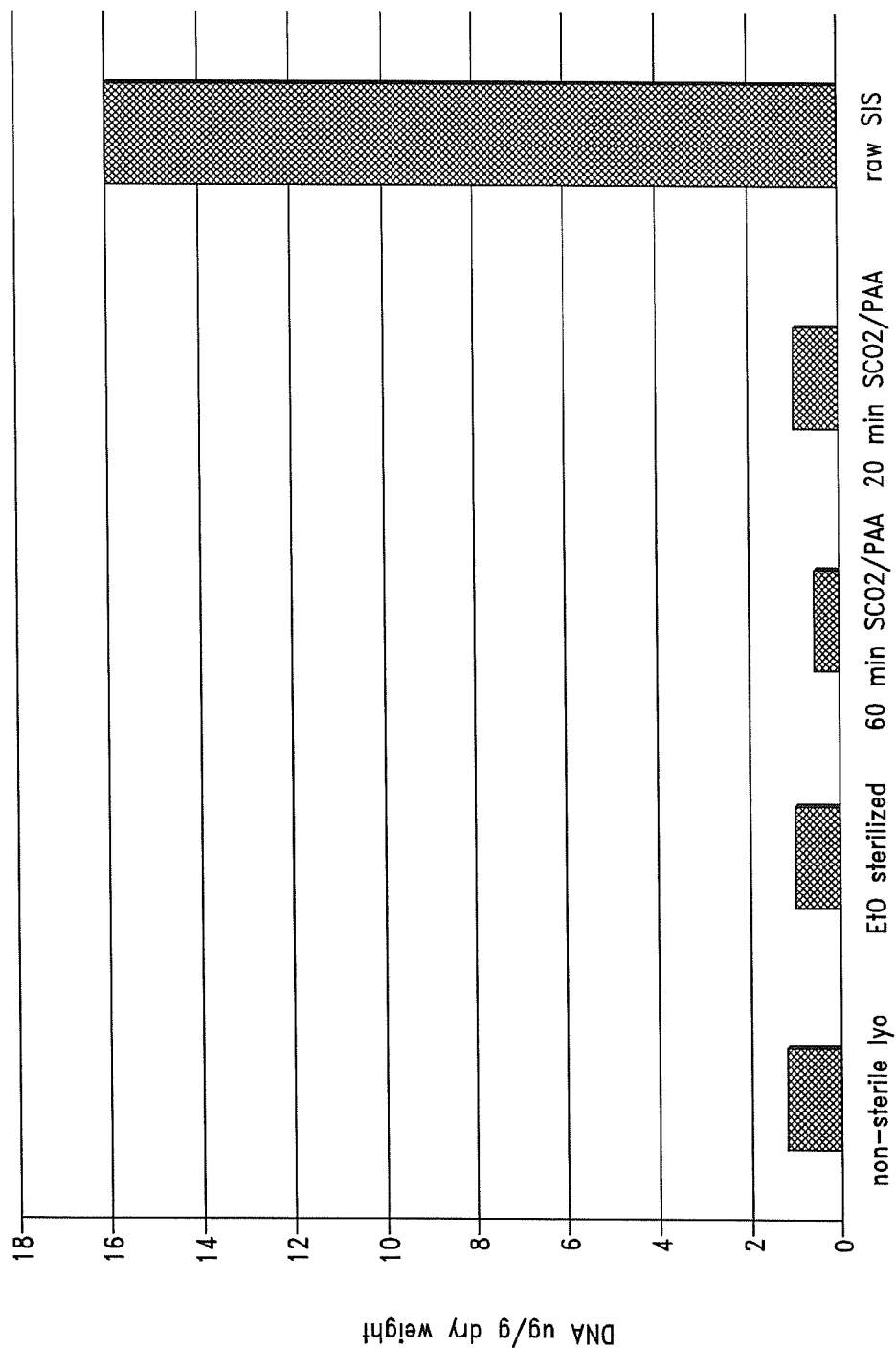
FIGS. 1-2 show the results of an experiment in which DNA content was measured for small intestinal submucosa (SIS) compositions following various sterilization methods, including the sterilization methods described herein.

The present invention may be understood more readily by reference to the following detailed description, examples, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the appended claims.

It is understood that the disclosed methods and compositions are not limited to the particular methodology, protocols, and reagents described, as these may vary. It is also to be understood that the terminology used herein is for the purpose of describing particular embodiments only and is not intended to limit the scope of the present invention which will be limited only by the appended claims.

A. DEFINITIONS

Unless defined otherwise, all technical and scientific terms used herein have the same meanings as commonly understood by one of skill in the art to which the disclosed methods and compositions belong. Although any methods and materials similar or equivalent to those described herein can be used in the practice or testing of the present methods and compositions, the particularly useful methods, devices, and materials are as described.

It must be noted that as used herein and in the appended claims, the singular forms "a," "an," and "the" include plural referents unless the context clearly dictates otherwise. Thus, for example, reference to "a compound" includes a plurality of such compounds; reference to "the compound" is a reference to one or more compounds and equivalents thereof known to those skilled in the art, and so forth.

The word "or" as used herein means any one member of a particular list and also includes any combination of members of that list.

"Optional" or "optionally" means that the subsequently described event, circumstance, or material may or may not occur or be present and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that the throughout the application, data are provided in a number of different formats and that these data represent endpoints, starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units is also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to" and is not intended to exclude, for example, other additives, components, integers or steps.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such disclosures by virtue of prior invention. No admission is made that any reference constitutes prior art. The discussion of references states what their authors assert, and applicants reserve the right to challenge the accuracy and pertinence of the cited documents.

A. METHODS

Disclosed herein are methods of treating or preventing a cardiac arrhythmia in a subject. The methods can comprise administering to the cardiac tissue of the subject a therapeutically effective amount of a composition comprising a mammalian extracellular matrix (ECM).

In some aspects, the mammalian ECM is derived from a native source. In some aspects, the mammalian ECM is produced in vitro using mammalian cells. In some aspects, the mammalian ECM is extracted directly from mammalian tissue/organs. In some aspects the composition comprising mammalian ECM further comprises synthetic ECM.

In some aspects, the composition comprising a mammalian ECM inhibits scar formation. In some aspects, the composition comprising a mammalian ECM promotes regeneration of damaged tissue. In some aspects, the composition comprising a mammalian ECM inhibits inflammation.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

By "prevent" or "preventing" is meant reducing the frequency or severity of a disease or condition. The term does not require an absolute preclusion of the disease or condition. Rather, this term includes decreasing the chance for disease occurrence. Thus, disclosed are methods of reducing the occurrence and/or severity of a cardiac arrhythmia in a subject, comprising administering to cardiac tissue of the subject a therapeutically effective amount of a composition comprising a mammalian ECM.

The term "therapeutically effective" means that the amount of the composition used is of sufficient quantity to ameliorate one or more causes, symptoms, or sequelae of a disease or disorder. Such amelioration only requires a reduction or alteration, not necessarily elimination, of the causes, symptoms, or sequelae of a disease or disorder.

As used herein, the term "cardiac tissue" includes the myocardium, epicardium, endocardium, and pericardium (the pericardial sac) of the heart. The term as used herein also refers to the great vessels leading to or from the heart. The term as used herein also refers to portions of the vagus nerve that innervate the heart.

Thus, in some aspects, the methods comprise administering a composition comprising a mammalian ECM to the heart of the subject. In some aspects, the methods comprise administering a composition comprising a mammalian ECM to the myocardium of the subject. The myocardium can be ventricular myocardium. The myocardium can be atrial myocardium. In some aspects, the methods comprise administering a composition comprising a mammalian ECM to the epicardium of the subject. In some aspects, the methods comprise administering a composition comprising a mammalian ECM to the endocardium of the subject. In some aspects, the methods comprise administering a composition comprising a mammalian ECM to the pericardium of the subject. In some aspects, the methods comprise administering a composition comprising a mammalian ECM into the space between the epicardium and the pericardium of the subject.

In some aspects, the methods comprise administering a composition comprising a mammalian ECM to a great vessel of the subject. In some aspects, the vessel is the superior vena cava, inferior vena cava, pulmonary vein, pulmonary artery, or aorta of the subject. For example, the method can comprise administering a composition comprising a mammalian ECM to the adventitia (external portion) of one or more of the great vessels. In some aspects, the method comprises administering a composition comprising a mammalian ECM to the cardiac circulation. Thus, the method comprises administering a composition comprising a mammalian ECM into a blood vessel or heart chamber.

Parasympathetic innervation of the heart is mediated by the vagus nerve. The right vagus innervates the sinoatrial (SA) node. Parasympathetic hyperstimulation predisposes those affected to bradyarrhythmias. The left vagus when hyperstimulated predisposes the heart to atrioventricular (AV) blocks. Thus, in some aspects, the methods comprise administering a composition comprising a mammalian ECM to a portion of the vagus nerve of the subject that innervates the heart.

As used herein, the term "subject" means any individual who is the target of administration. The subject can be a vertebrate, for example, a mammal. Thus, the subject can be a human. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. As used herein, the terms "patient" and "subject" can be used interchangeably.

In some aspects, the subject of the disclosed method has been identified as being at risk of developing a cardiac arrhythmia. In some aspects, the subject of the disclosed method has undergone heart surgery, including, but not limited to, open-heart surgery. In some aspects, the subject of the disclosed method has undergone multiple combined heart procedures, including, but not limited to, open heart procedures. In some aspects, the subject of the disclosed method has undergone heart valve surgery. In some aspects, the subject of the disclosed method is at least 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 years of age. In some aspects, the composition is administered to a subject who has had a myocardial infarction. In some aspects, the subject of the disclosed method has emphysema or chronic obstructive pulmonary disease. In some aspects, the subject of the disclosed method has a history of arrhythmia.

In some aspects, the disclosed method does not comprise administering a patch comprising small intestinal submucosa (SIS) to an opening in the pericardial sac of the heart. In some aspects, the disclosed method does not consist of administering a patch comprising small intestinal submucosa (SIS) to an opening in the pericardial sac of the heart. In some aspects, the mammalian ECM is not SIS. Thus, in some aspects, the composition comprising mammalian ECM does not consist of SIS. In some aspects, the composition comprising mammalian ECM is not a patch. In some aspects, the disclosed method does not comprise administering the composition comprising mammalian ECM as a patch to an opening in the pericardial sac of the heart. In some aspects, the cardiac tissue of the disclosed method is not pericardium. In some aspects, the disclosed method does not comprise administering the composition to the pericardium.

In other aspects, however, the disclosed method comprises administering a patch comprising small intestinal submucosa (SIS) to an opening in the pericardial sac of the heart. The compositions used in the disclosed methods can comprise one or more additional agents (i.e., additives) such as growth factors, cytokines, proteoglycans, glycosaminoglycans (GAGs), proteins, peptides, nucleic acids, small molecules, cells and pharmaceutical agents, such as statin drugs, corticosterioids, anti-arrhythmic drugs, nonsteroidal anti-inflammatory drugs, other anti-inflammatory compounds, nanoparticles, and metallic compounds. In other aspects, the disclosed method comprises administering a patch comprising small intestinal submucosa (SIS) to an opening in the pericardial sac of the heart, but the method further comprises additional steps.

Also disclosed herein is a method of treating or preventing a cardiac arrhythmia in a subject, comprising administering to cardiac tissue of the subject a therapeutically effective amount of a composition comprising a mammalian extracellular matrix and further comprising an anti-arrhythmic drug, a lipid-lowering drug, cells, a protein, or a combination thereof.

1. Cardiac Arrhythmia

Cardiac arrhythmia (also referred to as dysrhythmia) is a term for any of a large and heterogeneous group of conditions in which there is abnormal electrical activity in the heart. The heart beat (pulse) can be too fast or too slow and can be regular or irregular.

Some arrhythmias are life-threatening medical emergencies that can result in cardiac arrest and sudden death. Others cause symptoms such as an abnormal awareness of heart beat (palpitations) and can be merely annoying. Others may not be associated with any symptoms at all but predispose toward potentially life-threatening stroke or embolus.

The term sinus arrhythmia refers to a normal phenomenon of mild acceleration and slowing of the heart rate that occurs with breathing in and out. It is usually quite pronounced in children and steadily lessens with age. This can also present during meditation breathing exercises that involve deep inhaling and breath-holding patterns.

Each heart beat originates as an electrical impulse from a small area of tissue in the right atrium of the heart called the sinus node or sinoatrial (SA) node. The impulse initially causes both atria to contract and then activates the atrioventricular (or AV) node, which is normally the only electrical connection between the atria and the ventricles, or main pumping chambers. The impulse then spreads through both ventricles via the His Purkinje fibers causing a synchronized contraction of the ventricular myocardium.

A heart rate less than 60 beats per minute is a bradycardia. This can be caused by a slowed signal from the sinus node (termed sinus bradycardia), a pause in the normal activity of the sinus node (termed sinus arrest), or by blocking of the electrical impulse on its way from the atria to the ventricles (termed AV block or heart block). Heart block comes in varying degrees and severity. It can be caused by reversible poisoning of the AV node (with drugs that impair conduction) or by irreversible damage to the node.

A heart rate faster than 100 beats per minute is a tachycardia. Tachycardia can result in palpitation; however, tachycardia is not necessarily an arrhythmia. Increased heart rate is a normal response to physical exercise or emotional stress. This is mediated by the sympathetic nervous system's effect on the sinus node and is called sinus tachycardia. Other things that increase sympathetic nervous system activity in the heart include ingested or injected substances such as caffeine or amphetamines, and an overactive thyroid gland (hyperthyroidism). Heart rate can be increased with sympathomimetic drugs.

Tachycardia that is not sinus tachycardia usually results from the addition of abnormal impulses that can begin by one of three mechanisms: automaticity, re-entry or triggered activity.

Automaticity refers to a cardiac muscle cell firing off an impulse on its own. All of the cells in the heart have the ability to initiate an action potential; however, only some of these cells are designed to routinely trigger heart beats. These cells are found in the conduction system of the heart and include the SA node, AV node, Bundle of His and Purkinje fibers. The SA node is a single specialized location in the atrium which has a higher automaticity (a faster pacemaker) than the rest of the heart and therefore is usually responsible for setting the heart rate and initiating each heart beat. Any part of the heart that initiates an impulse without waiting for the SA node is called an ectopic focus and is by definition a pathological phenomenon. This can cause a single premature beat now and then, or, if the ectopic focus fires more often than the SA node, it can produce a sustained abnormal rhythm. Conditions that increase automaticity include sympathetic nervous system stimulation and hypoxia. The resulting heart rhythm depends on where the first signal begins. If it is the SA node, the rhythm remains normal but rapid; if it is an ectopic focus, many types of arrhythmia can result.

Re-entry arrhythmias occur when an electrical impulse recurrently travels in a tight circle within the heart, rather than moving from one end of the heart to the other and then stopping. Every cardiac cell is able to transmit impulses in every direction but can only do so once within a short period of time. Normally, the action potential impulse will spread through the heart quickly enough that each cell will only respond once. However, if conduction is abnormally slow in some areas, part of the impulse will arrive late and potentially be treated as a new impulse. Depending on the timing, this can produce a sustained abnormal circuit rhythm. Re-entry circuits are responsible for atrial flutter, most paroxysmal supraventricular tachycardias, and dangerous ventricular tachycardia. When an entire chamber of the heart is involved in multiple micro-reentry circuits and therefore quivering with chaotic electrical impulses, it is said to be in fibrillation.

Fibrillation can affect one or both atria (atrial fibrillation) or one or both ventricles (ventricular fibrillation). If left untreated, ventricular fibrillation (VF, or V-fib) can lead to death within minutes.

Triggered beats occur when problems at the level of the ion channels in individual heart cells result in abnormal propagation of electrical activity and can lead to sustained abnormal rhythm. Triggered beats are relatively rare but can result from the action of anti-arrhythmic drugs.

Arrhythmia can be classified by rate (physiological, tachycardia, bradycardia), or mechanism (automaticity, re-entry, fibrillation).

It is also appropriate to classify arrhythmia by site of origin. For example, atrial arrhythmias include premature atrial contractions (PACs), wandering atrial pacemaker, multifocal atrial tachycardia, atrial flutter, and atrial fibrillation (Afib). Junctional arrhythmias include supraventricular tachycardia (SVT), AV nodal re-entrant tachycardia (the most common cause of paroxysmal supraventricular tachycardia (PSVT)), junctional rhythm, junctional tachycardia, and premature junctional complex. Atrioventricular arrhythmias include AV re-entrant tachycardia (occurs when a re-entry circuit crosses between the atria and ventricles somewhere other than the AV node).

Ventricular arrhythmias include premature ventricular contractions (PVC) (sometimes called ventricular extra beats (VEBs)), accelerated idioventricular rhythm, monomorphic ventricular tachycardia, polymorphic ventricular tachycardia, and ventricular fibrillation.

Heart blocks (also known as AV blocks, the most common causes of bradycardia) include first degree heart block (PR interval greater than 200 msec in length on the surface ECG), second degree heart block (Types 1 and 2), and third degree heart block (also known as complete heart block).

Cardiac arrhythmias are often first detected by auscultation of the heartbeat with a stethoscope or by feeling peripheral pulses. These methods cannot usually diagnose specific arrhythmias but can give a general indication of the heart rate and whether it is regular or irregular. Not all of the electrical impulses of the heart produce audible or palpable beats; in many cardiac arrhythmias, the premature or abnormal beats do not produce an effective pumping action and are experienced as "skipped" beats.

The simplest specific diagnostic test for assessment of heart rhythm is the electrocardiogram (abbreviated ECG or EKG). A Holter monitor is an EKG recorded over a 24-hour period, to detect arrhythmias that can happen briefly and unpredictably throughout the day.

Sudden arrhythmia death syndrome (SADS) is a term used to describe sudden death due to cardiac arrest brought on by an arrhythmia. Often, the subject has no symptoms before dying suddenly. The most common cause of sudden death in the United States is coronary artery disease. Approximately 300,000 people die suddenly of this cause every year in the United States. SADS can also be caused by, for example, many inherited conditions and heart diseases that can affect young people.

In children, for example, viral myocarditis, long Q-T syndrome, Brugada syndrome, Catecholaminergic polymorphic ventricular tachycardia and hypertrophic cardiomyopathy, and arrhythmogenic right ventricular dysplasia can cause SADS.

In some aspects, a cardiac arrhythmia is atrial fibrillation or ventricular fibrillation.

1. Administration

In some aspects, the mammalian ECM is a patch in a form such as a sheet, plug, a laminate, a weave, a polymer matrix, a plurality of strands, a sponge, or one or more strips. As used herein, a "sponge" can be a resilient, absorbent, porous composition comprising fibers of ECM. In one aspect, the fibers can be interlacing. A sponge can be used to deliver one or more of the disclosed additional agents (i.e., additives) to heart tissue. Thus, in some aspects, the mammalian ECM is placed into direct contact with the cardiac tissue of a subject during heart surgery. In some aspects, the composition comprising a mammalian ECM is administered to an opening in the pericardial sac of the heart. In some aspects, the composition overlaps the opening in the pericardial sac. Thus, the composition comprising a mammalian ECM can be administered to the surgical opening of the pericardium during or after heart surgery. In another aspect, the mammalian ECM can be placed into contact with cardiac structures, such as the great vessels, e.g., aorta, pulmonary artery, pulmonary vein, superior vena cava, and inferior vena cava. In some aspects, the mammalian ECM composition, for example a sponge, can be sandwiched between and in contact with the epicardium and the inner wall of the pericardial sac.

Wherein the mammalian ECM is in a solid form such as a sheet, a plug, a laminate, a weave, a polymer matrix, a plurality of strands, a sponge, or one or more strips, the composition can be attached to the cardiac tissue using standard means available in the art. For example, the composition comprising mammalian ECM can be attached to the cardiac tissue with sutures, bioadhesives such as fibrin glue, staples, and the like.

The disclosed compounds and compositions comprising a mammalian ECM can be administered in any suitable manner. For example, the compositions can be administered parenterally (e.g., intramuscular injection), topically or the like. Thus, in some aspects, the composition comprising a mammalian ECM is injectable. The disclosed compositions can be injected into the cardiac tissue using ordinary means. For example, the composition comprising a mammalian ECM can be delivered to the cardiac tissue via a syringe or a cardiac or coronary catheter. Cardiac catheterization (heart cath) is the insertion of a catheter into a chamber or vessel of the heart. This can be done for both diagnostic and/or interventional purposes. Coronary catheterization is a subset of this technique, involving the catheterization of the coronary arteries.

Thus, in some aspects, the composition comprising a mammalian ECM can be injected into the myocardium of the heart. In some aspects, the composition comprising a mammalian ECM can be injected into the epicardium of the heart. In some aspects, the composition comprising a mammalian ECM can be injected into the endocardium of the heart. In some aspects, the composition comprising a mammalian ECM can be injected into the pericardium of the heart. In some aspects, the composition comprising a mammalian ECM can be injected between layers of the heart, e.g., between the pericardium and epicardium, between the epicardium and myocardium, and between the myocardium and endocardium.

In some aspects, the composition comprising a mammalian ECM can be administered to the atrial or ventricular septum of the subject. For example, in some aspects, the composition comprising a mammalian ECM can be administered to a ventricular septal defect. A ventricular septal defect (VSD) is a defect in the ventricular septum, the wall dividing the left and right ventricles of the heart. The ventricular septum consists of an inferior muscular and superior membranous portion and is extensively innervated with conducting cardiomyocytes. The membranous portion, which is close to the atrioventricular node, is most commonly affected in adults and older children. Congenital VSDs are collectively the most common congenital heart defects.

In some aspects, the composition comprising a mammalian ECM can be administered to an atrial septal defect (ASD). An ASD is a form of congenital heart defect that enables blood flow between the left and right atria via the interatrial septum. The interatrial septum is the tissue that divides the right and left atria. Without this septum, or if there is a defect in this septum, it is possible for blood to travel from the left side of the heart to the right side of the heart, or vice versa. Irrespective of interatrial communication bi-directions, this results in the mixing of arterial and venous blood. The mixing of arterial and venous blood may or may not be hemodynamically significant, if even clinically significant. This mixture of blood may or may not result in what is known as a "shunt." The amount of shunting present, if any, dictates hemodynamic significance (see Pathophysiology below). A "right-to-left-shunt" typically poses the more dangerous scenario (see Pathophysiology below).

The mammalian ECM can be in an aerosol form. Thus, in some aspects, the mammalian ECM can be sprayed on the cardiac tissue of the subject.

The mammalian ECM can be in a particulate form. Particulate mammalian ECM can be administered by injecting an emulsified composition, spraying, layering, packing, dusting, painting, or other similar types of application of the dry particulate, the liquid composition, or the semi-solid compositions.

In some aspects, the composition is administered to the epicardial surface of the heart. Thus, in some aspects, the composition is injected, sprayed, or attached to the epicardial surface of the heart.

The exact amount of the compositions required can vary from subject to subject, depending on the species, age, weight and general condition of the subject, and the severity of the disorder being treated. Thus, it is not possible to specify an exact amount for every composition. However, an appropriate amount can be determined by one of ordinary skill in the art using only routine experimentation given the teachings herein. Thus, effective dosages and schedules for administering the compositions can be determined empirically, and making such determinations is within the skill in the art. The dosage ranges for the administration of the compositions are those large enough to produce the desired effect in which the symptom or disorder is affected. The dosage should not be so large as to cause adverse side effects, such as unwanted cross-reactions, anaphylactic reactions, and the like. Generally, the dosage can vary with the age, condition, sex and extent of the disease in the patient, route of administration, or whether other drugs are included in the regimen and can be determined by one of skill in the art. Dosage can vary and can be administered in one or more dose administrations daily, for one or several days. Guidance can be found in the literature for appropriate dosages for given classes of pharmaceutical products.

Following administration of a disclosed composition for treating, inhibiting, or preventing a cardiac arrhythmia, the efficacy of the method can be assessed in various ways well known to the skilled practitioner. For example, one of ordinary skill in the art will understand that a composition disclosed herein is efficacious in treating a cardiac arrhythmia in a subject using an electrocardiogram.

The compositions disclosed herein can be administered prophylactically to subjects who are at risk for cardiac arrhythmia. The disclosed compositions and methods can also be used, for example, as tools to isolate and test new drug candidates for treating or preventing cardiac arrhythmia. The disclosed compositions can also be used in a variety of ways as research tools. Other uses are disclosed, apparent from the disclosure, and/or will be understood by those in the art.

1. Combination Therapy

The herein disclosed methods can further comprise treating the subject with conventional anti-arrhythmia therapies. For example, there are many classes of anti-arrhythmic medications with different mechanisms of action and many different individual drugs within these classes. Thus, the method can further comprise administering to the subject one or more anti-arrhythmic medications.

Some arrhythmias, e.g., atrial fibrillation, cause blood clotting within the heart and increase risk of embolus and stroke. Anticoagulant medications such as warfarin and heparin, and anti-platelet drugs such as aspirin can reduce the risk of clotting. Thus, the method can further comprise administering to the subject an anticoagulant.

Arrhythmias can also be treated electrically, by applying a shock across the heart, either externally to the chest wall or internally to the heart via implanted electrodes or intra-operatively. Cardioversion can be achieved either pharmacologically or via the application of a shock synchronized to the underlying heartbeat. It is used for treatment of supraventricular tachycardias. In elective cardioversion, the recipient is usually sedated or lightly anesthetized for the procedure. For example, atrial flutter can be treated by cardioversion. Thus, the method can further comprise treating the subject with cardioversion.

With synchronized cardioversion, a reversion shock is delivered by way of pads or paddles of a selected amount of electric current over a pre-defined number of milliseconds at the optimal moment in the cardiac cycle which corresponds to the R wave of the QRS complex on the ECG Timing the shock to the R wave prevents the delivery of the shock during the vulnerable period (or relative refractory period) of the cardiac cycle, which could induce ventricular fibrillation.

Defibrillation differs from cardioversion in that the shock is not synchronized to a cardiac cycle. It is needed for the chaotic rhythm of ventricular fibrillation and is also used for pulseless ventricular tachycardia. Often, more electricity is required for defibrillation than for cardioversion. Because most subjects with ventricular fibrillation are unconscious, there is generally no need for sedation. Thus, the method can further comprise treating the subject with defibrillation.

Defibrillation or cardioversion can be accomplished by an implantable cardioverter-defibrillator (ICD). Thus, the method can further comprise administering to the subject an ICD.

Electrical treatment of arrhythmia also includes cardiac pacing. Temporary pacing can be necessary for reversible causes of very slow heartbeats, or bradycardia, (for example, from drug overdose or myocardial infarction). A permanent pacemaker can be placed in situations where the bradycardia is not expected to recover. Thus, the method can further comprise administering to the subject a pacemaker.

Fine probes can in some aspects be inserted through the blood vessels to map electrical activity from within the heart. This allows abnormal areas of conduction to be located very accurately, and subsequently destroyed with heat, cold, electrical or laser probes.

A. COMPOSITIONS

A patch of mammalian ECM has been shown to act as a mechanical scaffold while the body recruits the necessary cells to remodel and repair the cardiac tissue. Disclosed herein is the surprising ability of mammalian ECM to additionally treat and/or prevent cardiac arrhythmia. Thus, disclosed herein are compositions comprising mammalian ECM for use in the disclosed method(s) for treating or preventing cardiac arrhythmia in a subject. The disclosed compositions can be natural or synthetic. The compositions can be de-cellularized or comprise cells such as stem cells.

The herein disclosed compositions comprising mammalian ECM can be in the form of, for example, a patch, an emulsion, an injectable solution, a gel, a fluid, a paste, a powder, a strand, a sponge, a strip, a spray, a vapor, an aerosol, a cream, or a coating. The composition can further comprise one or more additional components, including, for example, a cell, peptide, polypeptide, protein or other biological moieties. Where the composition is a patch, it can be in a form selected from a sheet, a laminate, a weave, a polymer matrix, a plurality of strands, a sponge, one or more strips, or a combination thereof.

The herein disclosed compositions comprising mammalian ECM can be made into a particulate and fluidized as described in U.S. Pat. No. 5,275,826 to Badylak, U.S. Pat. No. 6,579,538 to Spievack, and U.S. Pat. No. 6,933,326 to Griffey. Fluidized or emulsified compositions (the liquid or semi-solid forms) can be present at a certain concentration, for example at a concentration of extracellular matrix greater than about 0.001 mg/ml. The concentration of these liquid or semi-solid components of the extracellular matrix composition can be in a range from about 0.001 mg/ml to about 200 mg/ml. The concentrations can further be found in more specific ranges such as for example the following set of ranges: about 5 mg/ml to about 150 mg/ml, about 10 mg/ml to about 125 mg/ml, about 25 mg/ml to about 100 mg/ml, about 20 mg/ml to about 75 mg/ml, about 25 mg/ml to about 60 mg/ml, about 30 mg/ml to about 50 mg/ml, and about 35 mg/ml to about 45 mg/ml, and about 40 mg/ml. to about 42 mg/ml. This set of ranges is exemplary and not intended to be exhaustive. It is contemplated that any value within any of these specifically listed ranges is a reasonable and useful value for a concentration of a liquid, emulsion, gel, paste or other liquid or semi-solid component of the composition.

1. Mammalian Extracellular Matrix

Extracellular matrix materials act as a natural scaffold for repairing soft tissues in the body. Animal studies have shown that the original extracellular matrix material remodels and is replaced by host tissue. Mammalian ECM is a resorbable biomaterial which has been used successfully as a xenogenic tissue graft that induces constructive remodeling of a variety of animal tissues including blood vessels, urinary bladder, dura, abdominal wall, tendons and ligaments. Examples of mammalian ECM include small intestine submucosa (SIS), urinary bladder submucosa (UBS), stomach submucosa (SS), or liver basement membrane (LBM).

The remodeling process includes rapid neovascularization and abundant accumulation of mesenchymal and epithelial cells that support extensive deposition of a new extracellular matrix. The noncollagenous portion of, for example, the SIS extracellular matrix is composed of various glycoproteins, such as hyaluronic acid, heparin, dermatan and chondroitin sulfate A, as well as FGF-2 and TGF-β growth factors.

After processing, mammalian ECM can retain many of the endogenous proteins, which act as growth and differentiation factors. These factors stimulate the local environment to populate the mammalian ECM with cells that are then able to differentiate into the original tissue that the mammalian ECM is replacing.

Mammalian ECM is a scaffold matrix of polymerized "structural" proteins that fit into three groups: collagens, glycoproteins, and proteoglycans (which have glycosaminoglycan repeats throughout). These molecules actually polymerize to form the scaffold or matrix of proteins that exists in dynamic interaction with cells and closely placed functional proteins (either on the cells, or bound to a structural protein). Thus, mammalian ECM also includes within its matrix scaffold "functional" proteins that interact with the structural proteins and with migrating or recruited cells, such as stem cells. The matrix functional proteins also interact with protein-expressing cells during the life and maintenance of the matrix scaffold itself as it rebuilds and maintains its components. Some proteins can be both a structural and functional protein, depending on the protein's configuration and placement in the whole matrix.

The ECM of, for example, cardiac tissue is made up of collagen types I (predominant), III, IV, V, and VI, combined which are 92% of the dry weight of the matrix. The ECM of cardiac tissue is also made up of glycosaminoglycans (GAGs), which include chondroitin sulfate A and B, heparan, heparin, and hyaluronic acid. Glycoproteins such as fibronectin and entactin, proteoglycans such as decorin and perlecan, and growth factors such as transforming growth factor beta (TGF-β), fibroblast growth factor-2 (FGF-2) and vascular endothelial growth factor (VEGF) are key players in the activity of a myocardium regenerating matrix. Furthermore, the precise chemical constitution of the matrix appears to play a role in its function, including, for example, what collagen type is prevalent in the matrix. Thus, the outcome of any tissue regenerative processes can be determined by the structural and functional components of the matrix scaffold that form the basis of the regenerative process.

Facilitating cell adhesion functions in ECM are cell adhesion molecules (CAMs). The CAMs can either be available endogenously or added as an additional component of the composition. CAMs are glycoproteins lodged in the surface of the cell membrane or transmembrane connected to cytoskeletal components of the cell. Specific CAMs include cadherins that are calcium dependent, and more than 30 types are known. Also working as CAMs are integrins which are proteins that link the cytoskeleton of the cell in which they are lodged to the extracellular matrix or to other cells through alpha and beta transmembrane subunits on the integrin protein. Cell migration, embryogenesis, hemostasis, and wound healing are facilitated by the integrins in the matrix. Syndecans are proteoglycans that combine with ligands for initiating cell motility and differentiation. Immunoglobulins provide any necessary immune and inflammatory responses. Selectins promote cell-cell interactions.

i. Native Sources and Preparations

In some aspects, the mammalian ECM is derived from native source. Native extracellular matrix scaffolds and the proteins that form them can be found in their natural environment, i.e., the extracellular matrices of mammals. These materials can be prepared for use in mammals in tissue graft procedures.

In some aspects, the mammalian ECM is extracted from mammalian tissue/organs. For example, in some aspects, the mammalian ECM comprises the basement membrane (or transitional epithelial layer), tunica propria, tunica submucosa, tunica muscularis, tunica serosa, or a combination thereof from a mammalian tissue source. Thus, in some aspects, the mammalian ECM comprises the basement membrane (or transitional epithelial layer) from a mammalian tissue source. In some aspects, the mammalian ECM comprises the subjacent tunica propria from a mammalian tissue source. In some aspects, the mammalian ECM comprises the tunica submucosa from a mammalian tissue source. In some aspects, the mammalian ECM comprises the tunica muscularis from a mammalian tissue source. In some aspects, the mammalian ECM comprises the tunica serosa from a mammalian tissue source.

For example, small intestine submucosa (SIS) is described in U.S. Pat. No. 5,275,826; urinary bladder submucosa (UBS) is described in U.S. Pat. No. 5,554,389; stomach submucosa (SS) is described in U.S. Pat. No. 6,099,567; and liver basement membrane (LBM) is described in U.S. Pat. No. 6,379,710, each of which is incorporated herein by reference for teachings of how to make and use these native extracellular matrices.

Thus, in some aspects, the mammalian ECM of the disclosed compositions and methods is small intestine submucosa (SIS). In some aspects, the mammalian ECM of the disclosed compositions and methods is urinary bladder submucosa (UBS). In some aspects, the mammalian ECM of the disclosed compositions and methods is stomach submucosa (SS). In some aspects, the mammalian ECM of the disclosed compositions and methods is liver basement membrane (LBM).

In some aspects, the mammalian ECM of the disclosed compositions and methods is from dermis. For example, AlloDerm®, produced by LifeCell Corporation, is an acellular tissue matrix which is produced from normal human skin using processing techniques established to remove the epidermis and cells within the dermis without significantly altering the normal biochemistry and molecular architecture of the connective tissue matrix. The resulting product is in a freeze-dried form allowing extended shelf-life and ease of shipping without degradation or loss of the normal tissue matrix components. AlloDerm® can retain decorin, hyaluronic acid, chondroitin sulfates, nidogen, growth factors and other biochemical proteins present in normal soft tissues. Additionally, AlloDerm® can contain the basement membranes of vascular channels and the orientation of elastin and collagen fibers of the starting dermal tissue.

In some aspects, the mammalian ECM of the disclosed compositions and methods is from fascia. In some aspects, the mammalian ECM of the disclosed compositions and methods is from parenchymal tissue. In some aspects, the mammalian ECM of the disclosed compositions and methods is from pericardium. In some aspects, the mammalian ECM of the disclosed compositions and methods is myocardial extracellular matrix. In some aspects, the mammalian ECM of the disclosed compositions and methods is from decellularized heart tissue, produced, for example, by coronary artery perfusion with detergents (Ott, H C, et al. Nat. Med. 2008 February; 14(2):213-21).

In some aspects, the mammalian ECM comprises a collagen scaffold derived from a mammalian tissue or organ source. The collagen scaffold from mammalian source can in some aspects comprise the basement membrane of the mammalian tissue source.

In some aspects, the mammalian ECM is produced in vitro. For example, the mammalian ECM can be produced from culture of mammalian cells. The mammalian ECM can be produced from proteins extracted from mammalian tissue/organs. For example, in some aspects, the mammalian ECM comprises an artificial collagen scaffold synthesized from collagen extracted from a mammalian tissue or organ source. Collagen from mammalian sources can be retrieved from matrix-containing tissues and used to form a matrix composition. Extracellular matrices can be synthesized from cell cultures as in the product manufactured by Matrigel™. In addition, dermal extracellular matrix material, subcutaneous extracellular matrix material, large intestine extracellular matrix material, placental extracellular matrix material, omentum extracellular matrix material, heart extracellular matrix material, and lung extracellular matrix material, can be used, derived and preserved similarly as described herein for the SIS, SS, LBM, and UBS materials. Other organ tissue sources of basement membrane for use in accordance with the disclosed compositions and methods include, but are not limited to, spleen, lymph nodes, salivary glands, prostate, pancreas and other secreting glands. In general, any tissue of a mammal that has an extracellular matrix can be used for developing an extracellular matrix component.

Collagenous matrix can be selected from a variety of commercially available collagen matrices or can be prepared from a wide variety of natural sources of collagen. Collagenous matrix for use in accordance with the disclosed compositions and methods can comprise highly conserved collagens, glycoproteins, proteoglycans, and glycosaminoglycans in their natural configuration and natural concentration. Collagens can be from animal sources, from plant sources, or from synthetic sources, all of which are available and standard in the art.

The proportion of scaffold material in the composition when native scaffold is used can be large, as the natural balance of extracellular matrix proteins in the native scaffolds usually represents greater than 90% of the extracellular matrix material by dry weight. Thus, the scaffold component of the composition by weight can be generally greater than 50% of the total dry weight of the composition. The scaffold can comprise an amount of the composition by weight greater than 60%, greater than 70%, greater than 80%, greater than 82%, greater than 84%, greater than 86%, greater than 88%, greater than 90%, greater than 92%, greater than 94%, greater than 96%, and greater than 98% of the total composition.

Native extracellular matrices can be prepared with care that their bioactivity for treating or preventing cardiac arrhythmia is preserved to the greatest extent possible. Key functions that can be preserved include control or initiation of cell adhesion, cell migration, cell differentiation, cell proliferation, cell death (apoptosis), stimulation of angiogenesis, proteolytic activity, enzymatic activity, cell motility, protein and cell modulation, activation of transcriptional events, provision for translation events, inhibition of some bioactivities, for example inhibition of coagulation, stem cell attraction, and chemotaxis. Assays for determining these activities are standard in the art. For example, material analysis can be used to identify the molecules present in the material composition. Also, in vitro cell adhesion tests can be conducted to make sure that the fabric or composition is capable of cell adhesion.

The disclosed compositions comprising mammalian ECM can be decellularized in order to render them non-immunogenic. In some aspects, the decellularization process is completed with some of the key protein functions retained, either by replacement of proteins incidentally extracted with the cells, or by adding exogenous cells to the matrix composition after cell extraction, which cells produce or carry proteins involved in treating or preventing cardiac arrhythmia.

When adding proteins to the extracellular matrix composition, the proteins can be simply added with the composition, or each protein can be covalently linked to a molecule in the matrix. Standard protein-molecule linking procedures can be used to accomplish the covalent attachment.

For decellularization when starting with a source tissue/organ as a source of mammalian ECM, source tissue/organ perfusion process can be used. The source tissue/organ can be perfused with a decellularization agent, for example 0.1% peracetic acid, rendering the organ acellular. The source tissue/organ can then be cut into portions and stored (e.g., in aqueous environment, liquid nitrogen, cold, freeze-dried, or vacuum-pressed) for later use. Any appropriate decellularizing agent can be used in source tissue/organ perfusion process. Further, disclosed below is a method of sterilizing and simultaneously decellularizing more completely an ECM material for use in the disclosed methods for treating or preventing cardiac arrhythmia in a subject who has undergone heart surgery or had a myocardial infarction.

With regard to submucosal tissue, extractions can be carried out near neutral pH (in a range from about pH 5.5 to about pH 7.5) in order to preserve the presence of growth factors in the matrices. Alternatively, acidic conditions (i.e., less than pH 5.5) can be used to preserve the presence of glycosaminoglycan components, at a temperature in a range between 0 and 50 degrees centigrade. In order to regulate the acidic or basic environment for these aqueous extractions, a buffer and chaotropic agent (generally at a concentration from about 2M to about 8M) can be selected, such as urea (at a concentration from about 2M to 4M), guanidine (at a concentration from about 2M to about 6M, most typically about 4M), sodium chloride, magnesium chloride, and non-ionic or ionic surfactants. Urea at 2M in pH 7.4 provides extraction of FGF-2 and the glycoprotein fibronectin. Using 4M guanidine with pH 7.4 buffer yields a fraction having transforming growth factor beta. (TGF-$\beta$).

Because of the collagenous structure of basement membrane and the desire to minimize degradation of the membrane structure during cell dissociation, collagen specific enzyme activity can be minimized in the enzyme solutions used in the cell-dissociation step. For example, source tissue/organ can be treated with a calcium chelating agent or chaotropic agent, such as a mild detergent, e.g., as Triton 100. The cell dissociation step can also be conducted using a calcium chelating agent or chaotropic agent in the absence of an enzymatic treatment of the tissue/organ. The cell-dissociation step can be carried out by suspending source tissue slices in an agitated solution containing about 0.05 to about 2%, more typically about 0.1 to about 1% by weight protease, optionally containing a chaotropic agent or a calcium chelating agent in an amount effective to optimize release and separation of cells from the basement membrane without substantial degradation of the membrane matrix.

After contacting the source tissue/organ with the cell-dissociation solution for a time sufficient to release all cells from the matrix, the resulting tissue/organ basement membrane can be rinsed one or more times with saline and optionally stored in a frozen hydrated state or a partially dehydrated state until used as described below. The cell-dissociation step can require several treatments with the cell-dissociation solution to release substantially all cells from the basement membrane. The source tissue/organ can be treated with a protease solution to remove the component cells, and the resulting extracellular matrix material is further treated to remove or inhibit any residual enzyme activity. For example, the resulting basement membrane can be heated or treated with one or more protease inhibitors.

Basement membrane or other native extracellular matrix scaffolds can be sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly weaken the mechanical strength and biotropic properties of the material is preferably used. For example, it is believed that strong gamma radiation can cause loss of strength in the graft material. Example sterilization techniques include exposing the graft to peracetic acid, low dose gamma irradiation, gas plasma sterilization, and high-pressure/supercritical carbon dioxide.

Further disclosed below are methods of sterilizing and decellularizing the disclosed ECM compositions, whereby the methods not only do not significantly weaken the mechanical strength and bioptric properties of the ECM compositions, but also the methods are more effective in decellularizing the ECM compositions and in enhancing the incorporation of various additives into the ECM compositions. Thus, the disclosed sterilization and decellularization methods provide ECM compositions that are more decellularized and have a greater capacity to incorporate and then deliver more additives than ECM compositions known in the art.

ii. Synthetic ECM

Also disclosed are compositions comprising synthetic ECM for use in the disclosed methods. Synthetic ECM for use in the disclosed compositions and methods can be formed using synthetic molecules that polymerize much like native collagen and which form a scaffold environment that mimics the native environment of mammalian ECM scaffolds. Accordingly, such materials as polyethylene terephthalate fiber (Dacron®), polytetrafluoroethylene (PTFE), glutaraldehyde-cross linked pericardium, polylactate (PLA), polyglycol (PGA), hyaluronic acid, polyethylene glycol (PEG), polyethylene, nitinol, and collagen from non-animal sources (such as plants or synthetic collagens), can be used as components of a synthetic extracellular matrix scaffold. The synthetic materials listed are standard in the art, and forming hydrogels and matrix-like materials with them is also standard. Their effectiveness can be tested in vivo as disclosed earlier, by testing in mammals, along with components that typically constitute native extracellular matrices, particularly the growth factors and cells responsive to them.

The extracellular matrix-like materials are described generally in Rosso et al. (Journal of Cellular Physiology 199:174-180, 2004), which is incorporated by reference herein for the teachings of how to make and use these materials. In addition, some extracellular matrix-like materials are listed here. Particularly useful biodegradable and/or bioabsorbable polymers include polylactides, polyglycolides, polycarprolactone, polydioxane and their random and block copolymers. Examples of specific polymers include poly D,L-lactide, polylactide-co-glycolide (85:15) and polylactide-co-glycolide (75:25). The biodegradable and/or bioabsorbable polymers used in the fibrous matrix of the disclosed compositions and methods can have a molecular weight in the range of about 1,000 to about 8,000,000 g/mole, including about 4,000 to about 250,000 g/mole. The biodegradable and/or bioabsorbable fiberizable material can be a biodegradable and bioabsorbable polymer. Examples of suitable polymers can be found in Bezwada, Rao S. et al. (1997) Poly(p-Dioxanone) and its copolymers, in Handbook of Biodegradable Polymers, A. J. Domb, J. Kost and D. M. Wiseman, editors, Hardwood Academic Publishers, The Netherlands, pp. 29-61. The biodegradable and/or bioabsorbable polymer can contain a monomer selected from the group consisting of a glycolide, lactide, dioxanone, caprolactone, trimethylene carbonate, ethylene glycol and lysine. The material can be a random copolymer, block copolymer or blend of monomers, homopolymers, copolymers, and/or heteropolymers that contain these monomers. The biodegradable and/or bioabsorbable polymers can contain bioabsorbable and biodegradable linear aliphatic polyesters such as polyglycolide (PGA) and its random copolymer poly(glycolide-co-lactide-) (PGA-co-PLA). The FDA has approved these polymers for use in surgical applications, including medical sutures. An advantage of these synthetic absorbable materials is their degradability by simple hydrolysis of the ester backbone in aqueous environments, such as body fluids. The degradation products are ultimately metabolized to carbon dioxide and water or can be excreted via the kidneys. These polymers are very different from cellulose-based materials, which cannot be absorbed by the body.

Other examples of suitable biocompatible polymers are polyhydroxyalkyl methacrylates including ethylmethacrylate, and hydrogels such as polyvinylpyrrolidone, polyacrylamides, etc. Other suitable bioabsorbable materials are biopolymers which include collagen, gelatin, alginic acid, chitin, chitosan, fibrin, hyaluronic acid, dextran, polyamino acids, polylysine and copolymers of these materials. Any glycosaminoglycan (GAG) type polymer can be used. GAGs can include, e.g., heparin, chondroitin sulfate A or B, and hyaluronic acid, or their synthetic analogues. Any combination, copolymer, polymer or blend thereof of the above examples is contemplated for use according to the disclosed compositions and methods. Such bioabsorbable materials can be prepared by known methods.

Nucleic acids from any source can be used as a polymeric biomaterial. Sources include naturally occurring nucleic acids as well as synthesized nucleic acids. Nucleic acids suitable for use in the disclosed compositions and methods include naturally occurring forms of nucleic acids, such as DNA (including the A, B and Z structures), RNA (including mRNA, tRNA, and rRNA together or separated), and cDNA, as well as any synthetic or artificial forms of polynucleotides. The nucleic acids used in the disclosed compositions and methods can be modified in a variety of ways, including by cross linking, intra-chain modifications such as methylation and capping, and by copolymerization. Additionally, other beneficial molecules can be attached to the nucleic acid chains. The nucleic acids can have naturally occurring sequences or artificial sequences. The sequence of the nucleic acid can be irrelevant for many aspects of the disclosure. However, special sequences can be used to prevent any significant effects due to the information coding properties of nucleic acids, to elicit particular cellular responses or to govern the physical structure of the molecule. Nucleic acids can be used in a variety of crystalline structures both in finished biomaterials and during their production processes. Nucleic acid crystalline structure can be influenced by salts used with the nucleic acid. For example, Na, K, Bi, and Ca salts of DNA all have different precipitation rates and different crystalline structures. Additionally, pH influences crystalline structure of nucleic acids.

The physical properties of the nucleic acids can also be influenced by the presence of other physical characteristics. For example, inclusion of hairpin loops can result in more elastic biomaterials or can provide specific cleavage sites.

The nucleic acid polymers and copolymers produced can be used for a variety of tissue engineering applications, including to increase tissue tensile strength, improve wound healing, speed up wound healing, as templates for tissue formation, to guide tissue formation, to stimulate nerve growth, to improve vascularization in tissues, as a biodegradable adhesive, as device or implant coating, or to improve the function of a tissue or body part. The polymers can also more specifically be used as sutures, scaffolds and wound dressings. The type of nucleic acid polymer or copolymer used can affect the resulting chemical and physical structure of the polymeric biomaterial.

iii. Combinations

The herein disclosed compositions can comprise combinations of mammalian ECM from two or more sources or in two or more distinct forms. Thus, the disclosed compositions can comprise any combination of native and/or synthetic mammalian ECMs disclosed herein.

Thus, for example, the composition can comprise mammalian ECM combinations from such sources as, for example, but not limited to, small intestine submucosa, liver basement membrane, stomach submucosa, urinary bladder submucosa, placental basement membrane, pancreatic basement membrane, large intestine submucosa, lung interstitial membrane, respiratory tract submucosa, heart extracellular matrix, dermal matrix, and in general extracellular matrix from any mammalian fetal tissue. Any one of these tissue sources can provide extracellular matrix that can then be manipulated into a designated form (liquid, semi-solid, or solid form), for use in a composition.

The combinations of mammalian ECM from two or more sources can be mixed solids, mixed liquids, mixed suspensions, mixed emulsions, mixed gels, mixed pastes, or mixed solid particulates. All of these compositions are mixtures of extracellular matrices from two or more sources, for example mixtures of powders or particulates from two or more extracellular matrices, mixtures of pastes from two or more extracellular matrices, mixtures of suspensions from two or more extracellular matrices, mixtures of emulsions or gels from two or more extracellular matrices and mixtures of liquids from two or more extracellular matrices.

The compositions can be made from three mammalian tissue sources, four mammalian tissue sources, five mammalian tissue sources, six mammalian tissue sources, and conceivably up to ten or more tissue sources. These tissue sources can be from the same mammal (for example the same cow, the same pig, the same rodent, the same human, etc.), the same species of mammal (e.g. cow, pig, rodent, human), or different species of mammals (for example liver matrix from a pig, small intestine submucosa from a cow, and urinary bladder submucosa from a dog, all mixed together in the composition).

The compositions can comprise two or more liquid matrices (from different tissue sources) combined together. The composition can be two or more emulsion matrices (from different tissue sources) combined together. The composition can be two or more particulate matrices (from different tissue sources) combined together. The composition can be a liquid mixture of two or more extracellular matrices. The composition can be a suspension mixture of two or more extracellular matrices.

For example, a composition can comprise a combination of SIS in sheet, particulate, suspension, emulsion, gel or liquid form with SS, or LBM, or UBS in sheet, particulate, suspension, emulsion, gel or liquid form. For example, a composition can comprise a combination of SS in sheet, particulate, suspension, emulsion, gel or liquid form with SIS, or LBM, or UBS in sheet, particulate, suspension, emulsion, gel or liquid form. For example, a composition can comprise a combination of LBM in sheet, particulate, suspension, emulsion, gel or liquid form with SS, or SIS, or UBS in sheet, particulate, suspension, emulsion, gel or liquid form. For example, a composition can comprise a combination of UBS in sheet, particulate, suspension, emulsion, gel or liquid form with SS, or SIS, or LBM in sheet, particulate, suspension, emulsion, gel or liquid form.

The disclosed compositions can comprise combinations of mammalian ECM from one or more sources but in two or more distinct forms. For example, a composition can comprise a gel matrix combined with a particulate matrix. In some aspects, mammalian ECM in particulate form can be dusted onto mammalian ECM in a sheet form.

In some aspects, the composition can comprise a combination of SIS, SS, or LBM, or UBS in sheet, suspension, emulsion, gel or liquid form with SIS, SS, or LBM, or UBS in particulate four. In some aspects, the composition can comprise a combination of SIS, SS, or LBM, or UBS in particulate, suspension, emulsion, gel or liquid form with SIS, SS, or LBM, or UBS in sheet form. In some aspects, the composition can comprise a combination of SIS, SS, or LBM, or UBS in sheet, particulate, suspension, gel or liquid form with SIS, SS, or LBM, or UBS in emulsion form. In some aspects, the composition can comprise a combination of SIS, SS, or LBM, or UBS in sheet, particulate, suspension, emulsion, or liquid form with SIS, SS, or LBM, or UBS in gel form. In some aspects, the composition can comprise a combination of SIS, SS, or LBM, or UBS in sheet, particulate, suspension, emulsion, or gel form with SIS, SS, or LBM, or UBS in liquid form. In some aspects, the composition can comprise a combination of SIS, SS, or LBM, or UBS in sheet, particulate, liquid, emulsion, or gel form with SIS, SS, or LBM, or UBS in suspension form.

As disclosed herein, the composition comprising mammalian ECM can be prepared for preferred consistency. For example, mammalian ECM can be prepared as a combination of gel and particulate in a ratio optimal to prevent dissipation into the blood stream. For example, the composition comprising mammalian ECM can comprise about 40% ECM in gel form and about 60% ECM in dry particulate form. Thus, disclosed herein is a composition comprising mammalian ECM in both gel and dry particulate forms, wherein the gel form comprises about 10, 15, 20, 25, 30, 35, 36, 37, 38, 39, 40, 41, 42, 43, 44, 45, 50% of the ECM in the composition. Thus, the dry particulate form can comprise about 90, 85, 80, 75, 70, 65, 64, 63, 62, 61, 60, 59, 58, 57, 56, 55, 50% of the ECM in the composition.

Selection of the concentrations of the liquid or semi-solid compositions (liquids, gels, suspensions emulsions, or pastes) is important. For example, the liquid forms can be present in a range of concentrations, from very dilute at about 0.001 mg/ml to greater concentrations of up to about 200 mg/ml. The concentrations can further be found in more specific ranges such as, for example, the following set of ranges: from about 5 mg/ml to about 150 mg/ml, from about 10 mg/ml to about 125 mg/ml, from about 25 mg/ml to about 100 mg/ml, from about 20 mg/ml to about 75 mg/ml, from about 25 mg/ml to about 60 mg/ml, from about 30 mg/ml to about 50 mg/ml, from about 35 mg/ml to about 45 mg/ml, and from about 40 mg/ml to about 42 mg/ml. This set of ranges is exemplary and not intended to be exhaustive. It is contemplated that any value within any of these specifically listed ranges is a reasonable and useful value for a concentration of a liquid or semi-solid component of the composition.

The emulsion can be more concentrated than a liquid form and can retain a shape which can be useful in applying the matrix composition to certain parts of the body, hence its characterization as a "semi-solid". The emulsion can be concentrated enough to form shapes like a plug or other configuration suited to the site at which the matrix composition is being applied. Thick emulsion can be painted or otherwise applied at a site as a paste, and dusted with solid particulate on top of the emulsion. The solid particulate can be reconstituted to form the emulsion, or can be applied dry as a particulate powder which can dust a region in the subject being treated Dry particulate or reconstituted particulate that forms an emulsion of two or more mammalian ECM can be mixed together in some proportion. For example, 50% of SIS can be mixed with 50% of SS in a vial. This mixture can then be fluidized by hydrating it in a suitable buffer, for example saline. The hydration can be accomplished to a desired concentration of the mammalian ECM mixture, for example in a range from about 0.001 mg/ml to about 200 mg/ml. The concentrations can further be found in more specific ranges such as for example the following set of ranges: from about 5 mg/ml to about 150 mg/ml, from about 10 mg/ml to about 125 mg/ml, from about 25 mg/ml to about 100 mg/ml, from about 20 mg/ml to about 75 mg/ml, from about 25 mg/ml to about 60 mg/ml, from about 30 mg/ml to about 50 mg/ml, from about 35 mg/ml to about 45 mg/ml, and from about 40 mg/ml. to about 42 mg/ml. This set of ranges is exemplary and not intended to be exhaustive. It is contemplated that any value within any of these specifically listed ranges is a reasonable and useful value for a concentration of a liquid or semi-solid component of the composition.

The lower the concentration of extracellular matrix the more liquid the composition will be. The higher the concentration of extracellular matrix the more the composition approaches a gel-like emulsion or semi-solid consistency.

The ratio of the mixtures of the two (or more) extracellular matrices in any given composition from different sources (or the same source) can be unequal. So for example, LBM can be present at 75% and SIS can be present at 25%, i.e., a 3:1 ratio). Any suitable ratio can be used: 1:1, 1:2, 1:3, 1:4, 1:5, and so on. Where 3 or more tissue sources of extracellular matrix are represented in the composition, the same type of balance or imbalance in the amounts of the matrices can occur. For example, for extracellular matrix from 3 sources, each source can be present in equal proportions, i.e., 1:1:1 (33%/33%/33%). Alternatively, a disproportionate amount of the particulate can be from one source, e.g., 2:1:1 (50%/25%/25%). Likewise, all three sources can be present in disproportionate amounts, e.g., 50%/30%/20%.

The two or more mammalian ECMs can be fluidized (or emulsified) separately and the fluidized or emulsified compositions mixed together. As another alternative, the two or more mammalian ECMs can be fluidized or emulsified separately and administered separately. In addition, the two or more mammalian ECMs can remain in particulate solid form and be mixed together in a vial for administration as a solid combination particulate. Rehydration of a dry particulate mammalian ECM mixture can be accomplished just prior to use.

2. Proteins

The disclosed compositions comprising mammalian ECM can further comprise exogenous proteins, such as those normally found in mammalian ECM. The protein can be a collagen, a proteoglycan, a glycosaminoglycan (GAG) chain, a glycoprotein, a growth factor, a cytokine, a cell-surface associated protein, a cell adhesion molecule (CAM), an angiogenic growth factor, an endothelial ligand, a matrikine, a matrix metalloprotease, a cadherin, an immunoglobulin, a fibril collagen, a non-fibrillar collagen, a basement membrane collagen, a multiplexin, a small-leucine rich proteoglycan, decorin, biglycan, a fibromodulin, keratocan, lumican, epiphycan, a heparan sulfate proteoglycan, perlecan, agrin, testican, syndecan, glypican, serglycin, selectin, a lectican, aggrecan, versican, neurocan, brevican, cytoplasmic domain-44 (CD-44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-β), fibroblast growth factor-2 (FGF-2) (also called basic fibroblast growth factor (bFGF)), thrombospondin, osteopontin, angiotensin converting enzyme (ACE), or a vascular endothelial growth factor (VEGF). This list is not intended to be exhaustive.

Thus, the herein disclosed compositions comprising a mammalian ECM can comprise collagen I and III, elastin, laminin, CD44, hyaluronan, syndecan, bFGF, HGF, PDGF, VEGF, Fn, tenascin, heparin, heparan sulfate, chondroitin sulfate B, integrins, decorin, TGF-β, or a combination thereof.

2. Cells

In some aspects, the herein disclosed compositions comprising mammalian ECM further comprise one or more cells. In some aspects the cells are non-native, i.e., heterologous to the mammalian ECM. In some aspects the cells are autologous. In some aspects, the cells are stem cells. A non-exhaustive list of stem cells includes a human embryonic stem cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, an osteoblast, a chondrocyte, an exogenous cell, an endogenous cell, a stem cell, a hematopoietic stem cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a post-natal stem cell.

In some aspects, the stem cells have the potential to differentiate into cardiac tissue cells. Thus, in some aspects, the stem cells are pluripotent. In some aspects, the stem cells are angioblasts or hemangioblasts. In some aspects, the stem cells are myoblasts. Stem cells can be derived and maintained using standard methods for stem cell culture.

2. Pharmaceuticals

The herein disclosed compositions comprising mammalian ECM can further comprise any known or newly discovered substance that can be administered to the heart of a subject. For example, the herein disclosed compositions comprising mammalian ECM can further comprise an antiarrhythmic agent. Antiarrhythmic agents are a group of pharmaceuticals that are used to suppress fast and/or irregular rhythms of the heart (cardiac arrhythmias).

The Vaughan Williams classification, introduced in 1970, is one of the most widely used classification schemes for antiarrhythmic agents. This scheme classifies a drug based on the primary mechanism of its antiarrhythmic effect. There are five main classes in the Vaughan Williams classification of antiarrhythmic agents: Class I agents interfere with the sodium (Na+) channel; Class II agents are anti-sympathetic nervous system agents (most agents in this class are beta blockers); Class III agents affect potassium (K+) efflux; Class IV agents affect calcium channels and the AV node; and Class V agents work by other or unknown mechanisms.

Class Ia agents include Quinidine, Procainamide, and Disopyramide. Class Ib agents include Lidocaine, Phenyloin, and Mexiletine. Class Ic agents include Flecamide, Propafenone, and Moricizine. Class II agents include Propranolol, Esmolol, Timolol, Metoprolol, and Atenolol. Class III agents include Amiodarone, Sotalol, Ibutilide, and Dofetilide. Class IV agents include Verapamil, and Diltiazem. Class V agents include Adenosine and Digoxin.

Thus, the herein disclosed compositions comprising mammalian ECM can further comprise one or more of Quinidine, Procainamide, Disopyramide, Lidocaine, Phenyloin, Mexiletine, Flecamide, Propafenone, Moricizine, Propranolol, Esmolol, Timolol, Metoprolol, Atenolol, Amiodarone, Sotalol, Ibutilide, Dofetilide, Verapamil, Diltiazem, Adenosine and Digoxin.

The provided compositions can further comprise one or more antibiotics (e.g., Aminoglycosides, Cephalosporins, Chloramphenicol, Clindamycin, Erythromycins, Fluoroquinolones, Macrolides, Azolides, Metronidazole, Penicillins, Tetracyclines, Trimethoprim-sulfamethoxazole, and Vancomycin).

The provided compositions can further comprise one or more steroids (e.g., Andranes (e.g., Testosterone), Cholestanes (e.g., Cholesterol), Cholic acids (e.g., Cholic acid), Corticosteroids (e.g., Dexamethasone), Estraenes (e.g., Estradiol), and Pregnanes (e.g., Progesterone).

The provided compositions can further comprise one or more classes of narcotic and non-narcotic analgesics, including, but not limited to, Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, and Pentazocine.

The provided compositions can further comprise one or more anti-inflammatory agents, including, but not limited to, Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Morniflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflumate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triclonide, Triflumidate, Zidometacin, and Zomepirac Sodium.

The provided compositions can further comprise one or more lipid-lowering drugs. As used herein, the term "lipid-lowering drug" refers to a drug that can be administered to a subject to reduce the serum levels of various heart disease-associated lipids, including, but not limited to, cholesterol, low-density lipoprotein (LDL), very low-density lipoprotein (VLDL), and triglycerides.

For example, the lipid-lowering drugs can be statins including, but not limited to, Lovastatin, Simvastatin, Atorvastatin, Fluvastatin, Pravastatin, Rosuvastatin, Cervistatin, and Pitavastatin. It is contemplated that any statin drug, now known or developed in the future, having lipid-reducing and/or anti-inflammatory properties can be used in the compositions described herein.

The provided compositions can further comprise one or more anti-histaminic agents, including, but not limited to, Ethanolamines (like diphenhydramine carbinoxamine), Ethylenediamine (like tripelennamine pyrilamine), Alkylamine (like chlorpheniramine, dexchlorpheniramine, brompheniramine, triprolidine), astemizole, loratadine, fexofenadine, Bropheniramine, Clemastine, Acetaminophen, Pseudoephedrine, and Triprolidine.

The provided compositions can further comprise one or more antineoplastic drugs, including, but not limited to, Acivicin, Aclarubicin, Acodazole Hydrochloride, AcrQnine, Adozelesin, Aldesleukin, Altretamine, Ambomycin, Ametantrone Acetate, Aminoglutethimide, Amsacrine, Anastrozole, Anthramycin, Asparaginase, Asperlin, Azacitidine, Azetepa, Azotomycin, Batimastat, Benzodepa, Bicalutamide, Bisantrene Hydrochloride, Bisnafide Dimesylate, Bizelesin, Bleomycin Sulfate, Brequinar Sodium, Bropirimine, Busulfan, Cactinomycin, Calusterone, Caracemide, Carbetimer, Carboplatin, Carmustine, Carubicin Hydrochloride, Carzelesin, Cedefingol, Chlorambucil, Cirolemycin, Cisplatin, Cladribine, Crisnatol Mesylate, Cyclophosphamide, Cytarabine, Dacarbazine, Dactinomycin, Daunorubicin Hydrochloride, Decitabine, Dexormaplatin, Dezaguanine, Dezaguanine Mesylate, Diaziquone, Docetaxel, Doxorubicin, Doxorubicin Hydrochloride, Droloxifene, Droloxifene Citrate, Dromostanolone Propionate, Duazomycin, Edatrexate, Eflomithine Hydrochloride, Elsamitrucin, Enloplatin, Enpromate, Epipropidine, Epirubicin Hydrochloride, Erbulozole, Esorubicin Hydrochloride, Estramustine, Estramustine Phosphate Sodium, Etanidazole, Ethiodized Oil I 131, Etoposide, Etoposide Phosphate, Etoprine, Fadrozole Hydrochloride, Fazarabine, Fenretinide, Floxuridine, Fludarabine Phosphate, Fluorouracil, Fluorocitabine, Fosquidone, Fostriecin Sodium, Gemcitabine, Gemcitabine Hydrochloride, Gold Au 198, Hydroxyurea, Idarubicin Hydrochloride, Ifosfamide, Ilmofosine, Interferon Alfa-2a, Interferon Alfa-2b, Interferon Alfa-n1, Interferon Alfa-n3, Interferon Beta-I a, Interferon Gamma-Ib, Iproplatin, Irinotecan Hydrochloride, Lanreotide Acetate, Letrozole, Leuprolide Acetate, Liarozole Hydrochloride, Lometrexol Sodium, Lomustine, Losoxantrone Hydrochloride, Masoprocol, Maytansine, Mechlorethamine Hydrochloride, Megestrol Acetate, Melengestrol Acetate, Melphalan, Menogaril, Mercaptopurine, Methotrexate, Methotrexate Sodium, Metoprine, Meturedepa, Mitindomide, Mitocarcin, Mitocromin, Mitogillin, Mitomalcin, Mitomycin, Mitosper, Mitotane, Mitoxantrone Hydrochloride, Mycophenolic Acid, Nocodazole, Nogalamycin, Ormaplatin, Oxisuran, Paclitaxel, Pegaspargase, Peliomycin, Pentamustine, Peplomycin Sulfate, Perfosfamide, Pipobroman, Piposulfan, Piroxantrone Hydrochloride, Plicamycin, Plomestane, Porfimer Sodium, Porfiromycin, Prednimustine, Procarbazine Hydrochloride, Puromycin, Puromycin Hydrochloride, Pyrazofurin, Riboprine, Rogletimide, Safmgol, Safingol Hydrochloride, Semustine, Simtrazene, Sparfosate Sodium, Sparsomycin, Spirogermanium Hydrochloride, Spiromustine, Spiroplatin, Streptonigrin, Streptozocin, Strontium Chloride Sr 89, Sulofenur, Talisomycin, Taxane, Taxoid, Tecogalan Sodium, Tegafur, Teloxantrone Hydrochloride, Temoporfin, Teniposide, Teroxirone, Testolactone, Thiamiprine, Thioguanine, Thiotepa, Tiazofurin, Tirapazamine, Topotecan Hydrochloride, Toremifene Citrate, Trestolone Acetate, Triciribine Phosphate, Trimetrexate, Trimetrexate Glucuronate, Triptorelin, Tubulozole Hydrochloride, Uracil Mustard, Uredepa, Vapreotide, Verteporfin, Vinblastine Sulfate, Vincristine Sulfate, Vindesine, Vindesine Sulfate, Vinepidine Sulfate, Vinglycinate Sulfate, Vinleurosine Sulfate, Vinorelbine Tartrate, Vinrosidine Sulfate, Vinzolidine Sulfate, Vorozole, Zeniplatin, Zinostatin, and Zorubicin Hydrochloride.

The herein provided compositions can further comprise one or more radiosensitizers including, but not limited to, gemcitabine, 5-fluorouracil, pentoxifylline, and vinorelbine.

2. Carriers

The disclosed mammalian ECM can be combined, conjugated or coupled with or to carriers and other compositions to aid administration, delivery or other aspects of the ECM and their use. For convenience, such compositions are referred to herein as carriers. Carriers can, for example, be a small molecule, pharmaceutical drug, fatty acid, detectable marker, conjugating tag, nanoparticle, or enzyme.

The disclosed compositions can be used therapeutically in combination with a pharmaceutically acceptable carrier. By "pharmaceutically acceptable" is meant a material that is not biologically or otherwise undesirable, i.e., the material can be administered to a subject, along with the composition, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the composition, which matrices are in the form of shaped articles, e.g., films, liposomes or microparticles. It will be apparent to those persons skilled in the art that certain carriers may be more preferable depending upon, for example, the route of administration and concentration of composition being administered.

Pharmaceutical carriers are known to those skilled in the art. These most typically would be standard carriers for administration of drugs to humans, including solutions such as sterile water, saline, and buffered solutions at physiological pH.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

D. METHODS OF MAKING THE COMPOSITIONS

The compositions disclosed herein and the compositions necessary to perform the disclosed methods can be made using any method known to those of skill in the art for that particular reagent or compound unless otherwise specifically noted. For example, U.S. Pat. No. 5,275,826, U.S. Pat. No. 5,554,389, U.S. Pat. No. 6,099,567, and U.S. Pat. No. 6,379,710, are disclosed herein by reference for methods of making compositions comprising small intestine submucosa (SIS), urinary bladder submucosa (UBS), stomach submucosa (SS), and liver basement membrane (LBM), respectively.

E. METHODS OF STERILIZING THE COMPOSITIONS

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used herein, the term "acellular" is meant to describe extracellular matrix compositions that are at least 80% decellularized such that the extracellular matrix composition is 80% without cells and/or cellular remnants. In some exemplary aspects described herein, the term "acellular" can refer to extracellular matrix compositions that are at least 90% decellularized such that the extracellular matrix composition is at least 90% without cells and/or cellular remnants. In other exemplary aspects described herein, the term "acellular" can refer to extracellular matrix compositions that are at least 95% decellularized such that the extracellular matrix composition is at least 95% without cells and/or cellular remnants. In other exemplary aspects described herein, the term "acellular" can refer to extracellular matrix compositions that are at least 96% decellularized such that the extracellular matrix composition is at least 96% without cells and/or cellular remnants. In still other exemplary aspects described herein, the term "acellular" can refer to extracellular matrix compositions that are at least 97% decellularized such that the extracellular matrix composition is at least 97% without cells and/or cellular remnants. In further exemplary aspects described herein, the term "acellular" can refer to extracellular matrix compositions that are at least 98% decellularized such that the extracellular matrix composition is at least 98% without cells and/or cellular remnants. In still further exemplary aspects described herein, the term "acellular" can refer to extracellular matrix compositions that are at least 99% decellularized such that the extracellular matrix composition is at least 99% without cells and/or cellular remnants. Thus, as used herein, the term "acellular" can refer to extracellular matrix compositions that are decellularized at levels of 80%, 81%, 82%, 83%, 84%, 85%, 86%, 87%, 88%, 89%, 90%, 91%, 92%, 93%, 94%, 95%, 96%, 97%, 98%, 99%, 100%, and any percentages falling between these values.

As used herein, the term "additive" refers to materials that can be selectively incorporated into the disclosed ECM materials to impart predetermined properties to the sterilized, acellular ECM compositions disclosed herein. Such additives can include, for example and without limitation, growth factors, cytokines, proteoglycans, glycosaminoglycans (GAGS), proteins, peptides, nucleic acids, small molecules, cells and pharmaceutical agents, such as statin drugs, corticosterioids, anti-arrhythmic drugs, nonsteroidal anti-inflammatory drugs, other anti-inflammatory compounds, nanoparticles, and metallic compounds.

As used herein, the term "contemporaneously" refers to the simultaneous and/or overlapping occurrence of events, as well as the sequential occurrence of events within about thirty minutes before or after one another. Thus, if a first event occurs, then a second event can be said to have occurred contemporaneously with the first event if it occurred concurrently with the first event or within thirty minutes before or after the first event. For example, if a first method step is performed, then a second method step performed five minutes after the first method step can be said to be performed "contemporaneously" with the first method step. Similarly, if the second method step was performed ten minutes before performance of a third method step, then the second method step can be said to be performed "contemporaneously" with the third method step.

As used herein, the term "emulsion" refers to a mixture in which a first ECM material is dispersed within a second ECM material, with the first ECM material being immiscible with the second ECM material. The "emulsions" described herein can refer to either oil-in-water type emulsions or water-in-oil type emulsions.

As used herein, the term "suspension" refers to a mixture in which a solid ECM material, such as, for example and without limitation, particulate ECM, is dispersed (suspended) in a fluid ECM material, such as, for example and without limitation, ECM gel or ECM liquid.

As used herein, the term "supercritical" refers to a fluid state of a material when it is held at or above its critical temperature and critical pressure. When a material is held at or above its critical temperature and critical pressure, then it typically adopts functional properties of both a gas and a liquid and is said to function as a supercritical fluid. Thus, for example, when carbon dioxide is held at or above its critical temperature (31.1° C.) and its critical pressure (1,071 psi), it behaves as a supercritical carbon dioxide fluid and can, for example, exhibit the expansion properties of a gas while having the density of a liquid.

Described herein are sterilized, acellular extracellular matrix (ECM) compositions and methods for making such compositions. As described herein, the disclosed extracellular matrix compositions are formed by contemporaneously sterilizing and decellularizing an isolated ECM material. More particularly, the disclosed methods contemporaneously accomplish desired sterilization and decellularization of the isolated ECM material such that the native properties of the tissue composition are maintained and the ECM material is rendered sterile and acellular.

As further described herein, the disclosed methods make use of rapid depressurization of the ECM material to decellularize the ECM material. This rapid depressurization of the ECM material occurs at depressurization rates that are significantly higher than the depressurization rates applied in previously known methods. In addition to decellularizing the ECM material as described herein, the rapid depressurization of the ECM material also can be used to enhance the incorporation of desired sterilants and additives into the ECM material.

ECM Compositions

In exemplary aspects, a sterilized, acellular ECM composition can comprise any known ECM component or material, including, for example and without limitation, mucosal layers and components, submucosal layers and components, muscularis layers and components, and/or basement membrane layers and components. It is contemplated that a disclosed sterilized, acellular ECM composition can comprise an ECM material obtained from any mammalian tissue source, including, for example and without limitation, stomach tissue (e.g., stomach submucosa (SS)), small intestinal tissue (e.g., small intestinal submucosa (SIS)), large intestinal tissue, bladder tissue (e.g., urinary bladder submucosa (UBS)), liver tissue (e.g., liver basement membrane (LBM)), heart tissue (e.g., pericardium), lung tissue, kidney tissue, pancreatic tissue, prostate tissue, mesothelial tissue, fetal tissue, a placenta, a ureter, veins, arteries, tissue surrounding the roots of developing teeth, and tissue surrounding growing bone. It is further contemplated that a disclosed sterilized, acellular ECM composition can comprise an ECM material obtained from ECM components or materials of one or more mammals including, for example and without limitation, humans, cows, pigs, dogs, sheep, cats, horses, rodents, and the like. Thus, it is contemplated that a disclosed sterilized, acellular ECM composition can comprise ECM components or materials from two or more of the same mammalian species, such as, for example and without limitation, two or more cows, two or more pigs, two or more dogs, or two or more sheep. It is further contemplated that a disclosed sterilized, acellular ECM composition can comprise ECM components or materials from two or more different mammalian species, such as, for example and without limitation, a pig and a cow, a pig and a dog, a pig and a sheep, or a cow and a sheep. It is still further contemplated that a disclosed sterilized, acellular ECM composition can comprise ECM components or materials obtained from a first tissue source, such as, for example and without limitation, SIS, from a first mammal, as well as ECM components or materials obtained from a second tissue source, such as, for example and without limitation, SS, from a second mammal.

In various aspects, a disclosed sterilized, acellular ECM composition can be produced in any suitable shape, including, for example and without limitation, a substantially flat sheet, a cylindrical tube, a substantially spherical structure, or a multi-laminate structure. It is contemplated that a disclosed sterilized, acellular ECM composition can also be produced in any suitable form, including, for example and without limitation, a solid, liquid, gel, particulate, sponge, emulsion, or suspension form. In one exemplary aspect, it is contemplated that a disclosed sterilized, acellular ECM composition can comprise an outer layer of solid ECM material that encloses an inner layer of liquid, particulate, emulsion, suspension, and/or gel ECM material.

In another exemplary aspect, it is contemplated that a disclosed sterilized, acellular ECM composition can comprise one or more types of particulate ECM materials that are suspended within an ECM gel to form an ECM suspension. In this aspect, it is contemplated that the particulates within a disclosed ECM suspension can have a diameter ranging from about 5 µm to about 300 µm, with an average diameter ranging from about 90 µm to about 100 µm. It is further contemplated that the percentage of gel within a disclosed ECM suspension can range from about 5% to about 50%, while the percentage of particulate within a disclosed ECM suspension can range from about 50% to about 95%. Thus, it is contemplated that the percentage of gel within a disclosed ECM suspension can be about 10%, while the percentage of particulate within the ECM suspension can be about 90%. It is further contemplated that the percentage of gel within a disclosed ECM suspension can be about 15%, while the percentage of particulate within the ECM suspension can be about 85%. More preferably, the percentage of gel within a disclosed ECM suspension can range from about 20% to about 30%, while the percentage of particulate within a disclosed ECM suspension can range from about 70% to about 80%. Thus, in an exemplary aspect, the percentage of gel within a disclosed ECM suspension can be about 20%, while the percentage of particulate within the ECM suspension can be about 80%. In another exemplary aspect, the percentage of gel within a disclosed ECM suspension can be about 25%, while the percentage of particulate within the ECM suspension can be about 75%. In an additional exemplary aspect, the percentage of gel within a disclosed ECM suspension can be about 30%, while the percentage of particulate within the ECM suspension can be about 70%. Although the above ranges refer to particular beginning point values and end point values, it is contemplated that a disclosed ECM suspension can be formed from gel percentages and particulate percentages falling within any of the ranges disclosed above.

In a further aspect, it is contemplated that a disclosed ECM suspension can comprise sterilized, decellularized ECM. In exemplary aspects, the ECM gel of a disclosed ECM suspension can be a hydrolyzed ECM. In these aspects, it is contemplated that the ECM gel of a disclosed ECM suspension can comprise ECM that is greater than about 50% hydrolyzed, more preferably, greater than about 70% hydrolyzed, and, most preferably, greater than about 90% hydrolyzed. In one exemplary aspect, the ECM gel of a disclosed ECM suspension can comprise ECM that is about 100% hydrolyzed. It is still further contemplated that the ECM components of the suspension can comprise at least one of: glycoproteins, such as, for example and without limitation, fibronectin and laminin; glycosaminoglycans, such as, for example and without limitation, heparan, hyaluronic acid, and chondroitin sulfate; and growth factors, thereby providing additional bioavailability for native cellular components. It is contemplated that the ECM components of the suspension can provide a structural and biochemical microenvironment that promotes cell growth and stem cell attraction following implantation of a disclosed ECM suspension within a subject. It is further contemplated that the ECM gel of a disclosed ECM suspension can function as a bulking agent that preserves a desired biomechanical environment until the cells of the subject can begin producing their own ECM.

It is still further contemplated that the desired biomechanical environment that is preserved by the ECM gel can substantially correspond to a biomechanical environment in native tissue. Thus, it is contemplated that the ECM gel of a disclosed ECM suspension can have an elastic modulus that is substantially equal to the elastic modulus of a target site within a subject. In exemplary aspects, the elastic modulus of the ECM gel of a disclosed ECM suspension can range from about 5 kPa to about 50 kPa, and, more preferably, from about 10 kPa to about 15 kPa.

In one non-limiting exemplary aspect, it is contemplated that, when a disclosed ECM suspension is configured for injection at a target site on or within the heart of a subject, the elastic modulus of the ECM gel of the disclosed ECM suspension can be about 11.5 kPa, which is the elastic modulus of cardiac muscle. As used herein, the term "on or within the heart" refers to locations that are, for example and without limitation, on or within the pericardium, epicardium, myocardium, endocardium, ventricles, atria, aorta, pulmonary arteries, pulmonary veins, vena cavae, and the like. In another aspect, it is further contemplated that a disclosed ECM suspension can be injected at a target site on or within the heart of the subject to therapeutically prevent or reverse left ventricular wall negative remodeling that occurs following acute myocardial infarction and/or chronic coronary heart disease. As used herein, the term "negative remodeling" refers to the detrimental and/or undesired changes in the heart that occur in response to myocardial injury; such undesired changes include, for example and without limitation, alterations in myocyte biology, myocyte loss, extracellular matrix degradation, extracellular matrix replacement fibrosis, alterations in left ventricular chamber geometry, increased wall stress (afterload), afterload mismatch, episodic subendocardial hypoperfusion, increased oxygen utilization, sustained hemodynamic overloading, and worsening activation of compensatory mechanisms. It is still further contemplated that a disclosed ECM suspension can be injected at a target site on or within the heart of the subject to therapeutically treat heart failure.

In an exemplary aspect, it is contemplated that a disclosed ECM suspension can be injected at a target site on or within the heart of a subject, such as, for example and without limitation, on or within the pericardium, epicardium, myocardium, endocardium, ventricles, atria, aorta, and the like. Optionally, in one aspect, a disclosed ECM suspension can be injected in a grid-like pattern. In this aspect, it is contemplated that a disclosed ECM suspension can be injected as a first series of spaced, substantially parallel lines and a second series of spaced, substantially parallel lines that are substantially perpendicular to the first series of spaced, substantially parallel lines, thereby defining the grid-like pattern.

In another aspect, it is contemplated that a disclosed ECM suspension can be applied to a target site on or within the heart of a subject to create a film of a disclosed ECM suspension having a thickness ranging from about 0.1 mm to about 10 mm, more preferably, from about 1 mm to about 5 mm, and, most preferably, from about 2 mm to about 4 mm. In one exemplary aspect, it is contemplated that a disclosed ECM suspension can be applied to a target site on or within the heart of the subject to create a film of the ECM suspension having a thickness of about 3 mm.

In a further exemplary aspect, it is contemplated that a disclosed ECM suspension can be injected at a target site positioned within the myocardium or scar tissue of the heart of a subject. In this aspect, it is contemplated that a disclosed ECM suspension can be injected into the myocardium or scar tissue within the heart of the subject at a desired depth relative to an outer surface of the pericardium. It is further contemplated that the desired depth at which a disclosed ECM suspension is injected can range from about 0.5 mm to about 5 mm, more preferably, from about 1 mm to about 3 mm, and most preferably, from about 1.5 mm to about 2.5 mm. In one exemplary aspect, it is contemplated that the desired depth at which a disclosed ECM suspension is injected can be about 2 mm. In this aspect, it is contemplated that the desired depth at which a disclosed ECM suspension is injected can correspond to a position proximate the junction between the epicardium and the myocardium. It is further contemplated that the desired depth at which a disclosed ECM suspension is injected can correspond to a position proximate ischemic and/or inflamed and/or injured heart tissue. In an exemplary aspect, it is contemplated that the desired depth at which a disclosed ECM suspension is injected can correspond to a position proximate necrotic and/or infarcted myocardium.

In exemplary aspects, when a disclosed ECM suspension is to be injected at a target site within the myocardium and/or one or more chambers of the heart of a subject following the occurrence of a myocardial infarction, it is contemplated that the ECM suspension should be injected at the target site during one of two possible time periods: prior to full onset of the inflammatory response of the subject or after the inflammatory response of the subject has decreased. In one aspect, when the ECM suspension is injected at the target site prior to full onset of the inflammatory response of the subject, it is contemplated that the ECM suspension should be injected at the target site substantially immediately after occurrence of the myocardial infarction up to the time of therapeutic reperfusion and/or revascularization of the heart (using, for example, a coronary artery bypass graft or a stent). In another aspect, when the ECM suspension is injected at the target site after the inflammatory response of the subject has decreased, it is contemplated that the ECM suspension should be injected at the target site after the acute phase of the myocardial infarction, during which negatively remodeling and scar tissue formation occur. In various aspects, it is contemplated that, following injection of a disclosed ECM suspension on or within the heart of a subject, the ECM suspension will not disperse but will instead attract stem cells to the target site, thereby promoting desired positive remodeling of the heart. As used herein, the term "positive remodeling" refers to beneficial regeneration and/or restructuring of damaged heart tissue; such positive remodeling promotes growth of new cells while preserving the functionality of the heart and preventing formation of scar tissue.

Sterilization and Decellularization of the ECM Compositions

Optionally, it is contemplated that the disclosed extracellular matrix compositions can be sterilized using a known sterilization system, such as, for example and without limitation, the system described in U.S. Pat. No. 7,108,832, assigned to NovaSterilis, Inc., which patent is expressly incorporated herein by reference in its entirety. Thus, in some aspects, the system used to perform the disclosed methods can comprise a standard compressed storage cylinder and a standard air compressor used in operative association with a booster (e.g., a Haskel Booster AGT 7/30). In other aspects, the air compressor and booster can be replaced with a single compressor. In exemplary aspects, the compressed storage cylinder can be configured to receive carbon dioxide, and the booster can be a carbon dioxide booster.

The system can further comprise an inlet port, which allows one or more additives contained in a reservoir to be added to a reactor vessel through a valve and an additive line. As used herein, the term "reactor vessel" refers to any container having an interior space that is configured to receive an ECM material and permit exposure of the ECM material to one or more sterilants and additives, as disclosed herein. In exemplary aspects, the reactor vessel can be, without limitation, a basket, a bucket, a barrel, a box, a pouch, and other known containers. It is contemplated that the reactor vessel can be re-sealable. In one aspect, it is contemplated that the reactor vessel can be a syringe that is filled with an ECM material. In an exemplary aspect, the reactor vessel can be a pouch comprising Tyvek® packaging (E.I. du Pont de Nemours and Company).

It is contemplated that a selected primary sterilant, such as, for example and without limitation, carbon dioxide, can be introduced to the reactor vessel from a header line via a valve and a supply line. It is further contemplated that a filter, such as, for example and without limitation, a 0.5 μm filter, can be provided in the supply line to prevent escape of material from the vessel. In exemplary aspects, a pressure gauge can be provided downstream of a shut-off valve in the header line to allow the pressure to be visually monitored. A check valve can be provided in the header line upstream of the valve to prevent reverse fluid flow into the booster. In order to prevent an overpressure condition existing in the header line, a pressure relief valve can optionally be provided.

In one aspect, depressurization of the reactor vessel can be accomplished using an outlet line and a valve in communication with the reactor vessel. In this aspect, it is contemplated that the depressurized fluid can exit the vessel via the supply line, be filtered by a filter unit, and then be directed to a separator, where filtered fluid, such as carbon dioxide, can be exhausted via an exhaust line. It is further contemplated that valves can be incorporated into the various lines of the apparatus to permit fluid isolation of upstream components.

In one exemplary aspect, the reactor vessel can comprise stainless steel, such as, for example and without limitation, 316 gauge stainless steel. In another exemplary aspect, the reactor vessel can have a total internal volume sufficient to accommodate the materials being sterilized, either on a laboratory or commercial scale. For example, it is contemplated that the reactor vessel can have a length of about 8 inches, an inner diameter of about 2.5 inches, and an internal volume of about 600 mL. In additional aspects, the reactor vessel can comprise a vibrator, a temperature control unit, and a mechanical stirring system comprising an impeller and a magnetic driver. In one optional aspect, it is contemplated that the reactor vessel can contain a basket comprising 316 gauge stainless steel. In this aspect, it is contemplated that the basket can be configured to hold materials to be sterilized while also protecting the impeller and directing the primary sterilant in a predetermined manner.

It is contemplated that the reactor vessel can be operated at a constant pressure or under continual pressurization and depressurization (pressure cycling) conditions without material losses due to splashing or turbulence and without contamination of pressure lines via back-diffusion. It is further contemplated that the valves within the system can permit easy isolation and removal of the reactor vessel from the other components of the system. In one aspect, the top of the reactor vessel can be removed when depressurized to allow access to the interior space of the reactor vessel.

Optionally, the system can comprise a temperature control unit that permits a user to adjustably control the temperature within the reactor vessel.

In use, the disclosed apparatus can be employed in a method of producing a sterilized, acellular ECM composition, such as disclosed herein. However, it is understood that the disclosed apparatus is merely exemplary, and that any apparatus capable of performing the disclosed method steps can be employed to produce the sterilized, acellular ECM composition. Thus, the claimed method is in no way limited to a particular apparatus.

It is contemplated that significant reductions in colony-forming units (CFUs) can be achieved in accordance with the disclosed methods by subjecting an isolated ECM material to sterilization temperature and pressure conditions using a primary sterilant. Optionally, it is contemplated that the primary sterilant can be combined with one or more secondary sterilants to achieve desired sterilization. Optionally, it is further contemplated that selected additives can be incorporated into an ECM material to impart desired characteristics to the resulting ECM composition. It is still further contemplated that the disclosed methods can be employed to produce sterilized, acellular ECM compositions for implantation within the body of a subject.

As described herein, the disclosed methods make use of rapid depressurization of an isolated ECM material to render the ECM material acellular. This rapid depressurization of the ECM material occurs at depressurization rates that are significantly higher than the depressurization rates applied in previously known methods. In addition to rendering acellular the ECM material as described herein, the rapid depressurization of the ECM material also can be used to enhance the incorporation of desired sterilants and additives into the ECM material. Further, it is contemplated that the rapid depressurization of the ECM material can render the ECM material acellular while also improving retention of native growth factors, as compared to previously known decellularization methods. Still further, it is contemplated that the rapid depressurization of the ECM material can be used to improve retention of the tensile strength of the ECM material, as compared to previously known decellularization methods.

The disclosed methods not only do not significantly weaken the mechanical strength and bioptric properties of the ECM compositions, but also the methods are more effective in decellularizing the ECM compositions and in enhancing the incorporation of various additives into the ECM compositions. Thus, the disclosed sterilization and decellularization methods provide ECM compositions that are more decellularized and have a greater capacity to incorporate and then deliver more additives than ECM compositions known in the art. Moreover, the disclosed sterilization and decellularization methods provide ECM compositions that have greater amounts and/or concentrations of retained native growth factors and that have greater tensile strength than sterilized and decellularized ECM compositions known in the art.

In exemplary aspects, the primary sterilant can be carbon dioxide at or near its supercritical pressure and temperature conditions. However, it is contemplated that any conventional sterilant, including, for example, gas, liquid, or powder sterilants that will not interfere with the native properties of the ECM material, can be used as the primary sterilant.

In one exemplary aspect, the disclosed sterilization process can be practiced using carbon dioxide as a primary sterilant at pressures ranging from about 1,000 to about 3,500 psi and at temperatures ranging from about 25° C. to about 60° C. More preferably, when supercritical carbon dioxide is used, it is contemplated that the sterilization process can use carbon dioxide as a primary sterilant at pressures at or above 1,071 psi and at temperatures at or above 31.1° C. In this aspect, the ECM material to be sterilized can be subjected to carbon dioxide at or near such pressure and temperature conditions for times ranging from about 10 minutes to about 24 hours, more preferably from about 15 minutes to about 18 hours, and most preferably, from about 20 minutes to about 12 hours. Preferably, the carbon dioxide employed in the disclosed systems and methods can be pure or, alternatively, contain only trace amounts of other gases that do not impair the sterilization properties of the carbon dioxide. For ease of further discussion below, the term "supercritical carbon dioxide" will be used, but it will be understood that such a term is non-limiting in that carbon dioxide within the pressure and temperature ranges as noted above can be employed satisfactorily in the practice of the disclosed methods. Within the disclosed pressure and temperature ranges, it is contemplated that the carbon dioxide can be presented to the ECM material in a gas, liquid, fluid or plasma form.

The secondary sterilants employed in the disclosed methods can, in some aspects, include chemical sterilants, such as, for example and without limitation, peroxides and/or carboxylic acids. Preferred carboxylic acids include alkanecarboxylic acids and/or alkanepercarboxylic acids, each of which can optionally be substituted at the alpha carbon with one or more electron-withdrawing substituents, such as halogen, oxygen and nitrogen groups. Exemplary species of chemical sterilants employed in the practice of the disclosed methods include, for example and without limitation, hydrogen peroxide ($H_2O_2$), acetic acid (AcA), peracetic acid (PAA), trifluoroacetic acid (TFA), and mixtures thereof. In one exemplary aspect, the chemical sterilants can include Sporeclenz® sterilant, which is a mixture comprising acetic acid, hydrogen peroxide, and peracetic acid.

It is contemplated that the secondary sterilants can be employed in a sterilization-enhancing effective amount of at least about 0.001 vol. % and greater, based on the total volume of the primary sterilant. It is further contemplated that the amount of secondary sterilant can be dependent upon the particular secondary sterilant that is employed. Thus, for example, it is contemplated that peracetic acid can be present in relatively small amounts of about 0.005 vol. % and greater, while acetic acid can be employed in amounts of about 1.0 vol. % and greater. Thus, it is contemplated that the concentration of the secondary sterilants can range from about 0.001 vol. % to about 2.0 vol. % and can typically be used as disclosed herein to achieve a sterilization-enhancing effect in combination with the disclosed primary sterilants, such as, for example and without limitation, supercritical carbon dioxide.

In one aspect, the method of producing a sterilized, acellular ECM composition can comprise harvesting a selected tissue from a mammal and rinsing the selected tissue in sterile saline or other biocompatible liquid, including, for example and without limitation, Ringer's solution or a balanced biological salt solution. In this aspect, the selected tissue can be, for example and without limitation, stomach tissue (e.g., stomach submucosa (SS)), small intestinal tissue (e.g., small intestinal submucosa (SIS)), large intestinal tissue, bladder tissue (e.g., urinary bladder submucosa (UBS)), liver tissue (e.g., liver basement membrane (LBM)), heart tissue (e.g., pericardium, epicardium, endocardium, myocardium), lung tissue, kidney tissue, pancreatic tissue, prostate tissue, mesothelial tissue, fetal tissue, a placenta, a ureter, veins, arteries, heart valves with or without their attached vessels, tissue surrounding the roots of developing teeth, and tissue surrounding growing bone. In another aspect, the method can comprise freezing the selected tissue for a period ranging from about 12 to about 36 hours, more preferably, from about 18 to about 30 hours, and most preferably, from about 22 to about 26 hours. For example, it is contemplated that the period during which the selected tissue is frozen can be 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, and any other period of time falling between the preceding values. In an additional aspect, the method can comprise thawing the selected tissue in cold hypotonic tris buffer. Optionally, in this aspect, the method can comprise thawing the selected tissue in cold hypotonic tris buffer on ice with 5 mM ethylenediaminetetraacetic acid (EDTA). In exemplary aspects, it is contemplated that the steps of freezing and thawing the selected tissue can be cyclically repeated up to six times.

In another aspect, the method can comprise isolating an ECM material from the selected tissue. In this aspect, the ECM material can be any material comprising known extracellular matrix components, including, for example and without limitation, stomach tissue (e.g., stomach submucosa (SS)), small intestinal tissue (e.g., small intestinal submucosa (SIS)), large intestinal tissue, bladder tissue (e.g., urinary bladder submucosa (UBS)), liver tissue (e.g., liver basement membrane (LBM)), heart tissue (e.g., pericardium, epicardium, endocardium, myocardium), lung tissue, kidney tissue, pancreatic tissue, prostate tissue, mesothelial tissue, fetal tissue, a placenta, a ureter, veins, arteries, heart valves with or without their attached vessels, tissue surrounding the roots of developing teeth, and tissue surrounding growing bone. In one exemplary, non-limiting aspect, the step of isolating an ECM material can comprise isolating SIS from a mammalian tissue source. In this aspect, the method can comprise: incising a wall of a small intestine along a path that is substantially parallel to the longitudinal axis of the small intestine; opening the small intestine along the path of the incision such that the small intestine lies flat on a surface; rinsing the small intestine with sterile saline or other biocompatible fluid; mechanically stripping the SIS of the small intestine from the surrounding smooth muscle and serosal layers and from the tunica mucosa, leaving essentially the submucosal and basement membrane layers. However, it is contemplated that the ECM material can be isolated using any conventional technique, including those described in: U.S. Pat. No. 4,902,508; U.S. Pat. No. 5,275,826; U.S. Pat. No. 5,281,422; U.S. Pat. No. 5,554,389; U.S. Pat. No. 6,579,538; U.S. Pat. No. 6,933,326; U.S. Pat. No. 7,033,611; Voytik-Harbin et al., "Identification of Extractable Growth Factors from Small Intestinal Submucosa," J. Cell. Biochem., Vol. 67, pp. 478-491 (1997); Hodde et al., "Virus Safety of a Porcine-Derived Medical Device: Evaluation of a Viral Inactivation Method," Biotech. & Bioeng., Vol. 79, No. 2, pp. 211-216 (2001); Badylak et al., "The Extracellular Matrix as a Scaffold for Tissue Reconstruction," Cell & Developmental Biology, Vol. 13, pp. 377-383 (2002); Robinson et al., "Extracelular Matrix Scaffold for Cardiac Repair," Circulation, Vol. 112, pp. I-135-I-143 (2005); Hodde et al., "Effects of Sterilization on an Extracellular Matrix Scaffold: Part I. Composition and Matrix Architecture," J. Mater. Sci.: Mater. Med., Vol. 18, pp. 537-543 (2007); and Hodde et al., "Effects of Sterilization on an Extracellular Matrix Scaffold: Part II. Bioactivity and Matrix Interaction," J. Mater. Sci.: Mater. Med., Vol. 18, pp. 545-550 (2007), each of which is expressly incorporated herein by reference in its entirety.

In an additional aspect, the method can comprise incubating the isolated ECM material for 24 to 48 hours in 0.5-1% Triton X-100/0.5-1% Deoxycholic acid with 5 mM EDTA in Dulbecco's Phosphate Buffered Saline (DPBS) (Lonza Walkersville, Inc.). In this aspect, it is contemplated that flat or sheet-like ECM materials, such as stomach submucosa (SS), small intestinal submucosa (SIS), and urinary bladder submucosa (UBS), can be incubated in a stretched configuration. It is further contemplated that ECM material conduits or other lumenal ECM materials, such as ureters, arteries, veins, and tubular SIS, can be perfused with the various disclosed solutions through soaking and by use of a peristaltic pump.

In a further aspect, after incubation, the method can comprise rinsing the ECM material with DPBS. In this aspect, it is contemplated that the step of rinsing the ECM material can comprise rinsing the ECM material up to six times, including one, two, three, four, five, or six times, with each rinse lasting for about thirty minutes. In an exemplary aspect, it is contemplated that the step of rinsing the ECM material can comprise rinsing the ECM material three times, with each rinse lasting for about thirty minutes.

Optionally, in exemplary aspects, the method can further comprise a second incubation procedure. In these aspects, the second incubation procedure can comprise incubating the ECM material in isotonic tris buffer containing 10-50 µg/mL of RNAase/0.2-0.5 µg/mL DNAase with 5 mM EDTA. It is contemplated that the step of incubating the ECM material in isotonic tris buffer can be performed at a temperature of about 37° C., substantially corresponding to the temperature of a human body. It is further contemplated that the step of incubating the ECM material in isotonic tris buffer can be performed for a period ranging from about 30 minutes to about 24 hours, more preferably, from about 1 hour to about 18 hours, and most preferably, from about 2 hours to about 12 hours. In an additional aspect, the second incubation procedure can further comprise rinsing the ECM material with DPBS. In this aspect, it is contemplated that the step of rinsing the ECM material can comprise rinsing the ECM material three times, with each rinse lasting for about thirty minutes.

In yet another aspect, whether or not the second incubation procedure is performed, the method can comprise storing the ECM material at a temperature ranging from about 1° C. to about 10° C., more preferably, from about 2° C. to about 6° C., and, most preferably, from about 3° C. to about 5° C. In an exemplary aspect, the ECM material can be stored at 4° C.

In an additional aspect, the method can comprise introducing the ECM material into the interior space of a reactor vessel. Optionally, in this aspect, one or more secondary sterilants from the reservoir can be added into the interior space of the reactor vessel along with the ECM material. In these aspects, it is contemplated that the one or more secondary sterilants from the reservoir can be added into the interior space of the reactor vessel before, after, or contemporaneously with the ECM material. It is further contemplated that the temperature control unit can be selectively adjusted to produce a desired temperature within the interior space of the reactor vessel. In a further aspect, the method can comprise equilibrating the pressure within the reactor vessel and the pressure within the storage cylinder. For example, in this aspect, it is contemplated that the pressure within the reactor vessel and the pressure within the storage cylinder can be substantially equal to atmospheric pressure. In yet another aspect, after equilibration of the pressures within the apparatus, the method can comprise operating the magnetic driver to activate the impeller of the reactor vessel. In still a further aspect, the method can comprise selectively introducing the primary sterilant from the storage cylinder into the reactor vessel until a desired pressure within the reactor vessel is achieved. In this aspect, it is contemplated that the step of selectively introducing the primary sterilant into the reactor vessel can comprise selectively activating the air compressor and the booster to increase flow of the primary sterilant into the reactor vessel. In exemplary aspects, the air compressor and booster can be activated to subject the ECM material to supercritical pressures and temperatures, such as, for example and without limitation, the pressures and temperatures necessary to produce supercritical carbon dioxide, for a time period ranging from about 20 minutes to about 60 minutes.

In a further aspect, the method can comprise rapidly depressurizing the reactor vessel. In this aspect, a predetermined amount of primary sterilant, such as, for example and without limitation, supercritical carbon dioxide, can be released from the reactor vessel through the depressurization line. It is contemplated that the primary sterilant can be released from the reactor vessel through opening of the valve coupled to the reactor vessel to thereby rapidly reduce the pressure within the reactor vessel. As used herein, the term "rapid depressurization" refers to depressurization of the reactor vessel at a rate greater than or equal to 400 psi/min. For example, it is contemplated that the reactor vessel can be depressurized at a depressurization rate ranging from about 2.9 MPa/min. to about 18.0 MPa/min. (about 420 psi/min. to about 2,610 psi/min.), more preferably from about 5.0 MPa/min. to about 10.0 MPa/min. (725 psi/min. to about 1,450 psi/min.), and, most preferably, from about 7.0 MPa/min. to about 8.0 MPa/min. (about 1,015 psi/min. to about 1,160 psi/min.). Thus, these rapid depressurizations are significantly greater than the 300 psi/min. depressurization rate disclosed in U.S. Pat. No. 7,108,832. Without being bound by any particular theory, it is believed that the disclosed rapid depressurization rates increase the level of decellularization achieved in the ECM material. For example, the rapid depressurization of a disclosed ECM material can lead to levels of decellularization in the ECM material of greater than about 96%, including 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9%, and 100.0%.

In exemplary aspects, the method can further comprise the step of incorporating one or more additives into the ECM material. In these aspects, it is contemplated that the one or more additives can be provided in either a powder or a liquid form. In one optional aspect, the step of incorporating the one or more additives can comprise introducing the one or more additives into the reactor vessel during the step of rapidly depressurizing the reactor vessel. In this aspect, it is contemplated that the introduction of the one or more additives can be characterized as a conventional foaming process. In another optional aspect, the step of incorporating the one or more additives can comprise introducing the one or more additives into the reactor vessel after the step of rapidly depressurizing the reactor vessel. In this aspect, it is contemplated that the one or more additives can be added to the ECM material after the rapid depressurization of the reactor vessel has caused the ECM material to swell and/or expand, thereby permitting enhanced penetration of the additives into the ECM material. It is further contemplated that, in an exemplary aspect, the one or more additives can be added to the ECM material within about thirty minutes after the rapid depressurization of the reactor vessel. In a further optional aspect, the step of incorporating the one or more additives can comprise introducing the one or more additives into the reactor vessel both during and after the step of rapidly depressurizing the reactor vessel. In this aspect, it is contemplated that the one or more additives can be released into the reactor vessel in both a quick manner and a slow, extended manner. In still a further optional aspect, the step of incorporating the one or more additives can comprise introducing the one or more additives into the reactor vessel before the step of rapidly depressurizing the reactor vessel.

The disclosed additives can be incorporated into the ECM material to impart selected properties to the resulting sterilized, acellular ECM composition. Thus, it is contemplated that the one or more additives can be selected to replace or supplement components of the ECM material that are lost during processing of the ECM material as described herein. For example, and as described below, the one or more additives can comprise growth factors, cytokines, proteoglycans, glycosaminoglycans (GAGS), proteins, peptides, nucleic acids, small molecules, drugs, or cells. It is further contemplated that the one or more additives can be selected to incorporate non-native components into the ECM material. For example, the one or more additives can comprise, for example and without limitation, growth factors for recruiting stem cells, angiogenic cytokines, and anti-inflammatory cytokines. It is still further contemplated that the one or more additives can be pharmaceutical agents, such as statins, corticosteroids, non-steroidal anti-inflammatory drugs, anti-inflammatory compounds, anti-arrhythmic agents, and the like. It is still further contemplated that the one or more additives can be nanoparticles, such as, for example and without limitation, silver nanoparticles, gold nanoparticles, platinum nanoparticles, iridium nanoparticles, rhodium nanoparticles, palladium nanoparticles, copper nanoparticles, zinc nanoparticles, and other metallic nanoparticles. It is still further contemplated that the one or more additives can be metallic compounds. In one exemplary aspect, the one or more additives can be selected to pharmaceutically suppress the immune response of a subject following implantation of the resulting ECM composition into the body of a subject.

In one aspect, the one or more additives can comprise one or more growth factors, including, for example and without limitation, transforming growth factor-β-1, -2, or -3 (TGF-β-1, -2, or -3), fibroblast growth factor-2 (FGF-2), also known as basic fibroblast growth factor (bFGF), vascular endothelial growth factor (VEGF), placental growth factor (PGF), connective tissue growth factor (CTGF), hepatocyte growth factor (HGF), Insulin-like growth factor (IGF), macrophage colony stimulating factor (M-CSF), platelet derived growth factor (PDGF), epidermal growth factor (EGF), and transforming growth factor-α (TGF-α).

In another aspect, the one or more additives can comprise one or more cytokines, including, for example and without limitation, stem cell factor (SCF), stromal cell-derived factor-1 (SDF-1), granulocyte macrophage colony-stimulating factor (GM-CSF), interferon gamma (IFN-gamma), Interleukin-3, Interleukin-4, Interleukin-10, Interleukin-13, Leukemia inhibitory factor (LIF), amphiregulin, thrombospondin 1, thrombospondin 2, thrombospondin 3, thrombospondin 4, thrombospondin 5, and angiotensin converting enzyme (ACE).

In an additional aspect, the one or more additives can comprise one or more proteoglycans, including, for example and without limitation, heparan sulfate proteoglycans, betaglycan, syndecan, decorin, aggrecan, biglycan, fibromodulin, keratocan, lumican, epiphycan, perlecan, agrin, testican, syndecan, glypican, serglycin, selectin, lectican, versican, neurocan, and brevican.

In a further aspect, the one or more additives can comprise one or more glycosaminoglycans, including, for example and without limitation, heparan sulfate, hyaluronic acid, heparin, chondroitin sulfate B (dermatan sulfate), and chondroitin sulfate A.

In still a further aspect, the one or more additives can comprise one or more proteins, peptides, or nucleic acids, including, for example and without limitation, collagens, elastin, vitronectin, versican, laminin, fibronectin, fibrillin-1, fibrillin-2, plasminogen, small leucine-rich proteins, cell-surface associated protein, cell adhesion molecules (CAMs), a matrikine, a matrix metalloproteinase (MMP), a cadherin, an immunoglobin, a multiplexin, cytoplasmic domain-44 (CD-44), amyloid precursor protein, tenascin, nidogen/entactin, fibulin I, fibulin II, integrins, transmembrane molecules, and osteopontin.

In yet another aspect, the one or more additives can comprise one or more pharmaceutical agents, including, for example and without limitation, statin drugs, for example, cerevastatin, atorvastatin, fluvastatin, lovastatin, mevastatin, pitavastatin, pravastatin, rosuvastatin, and simvastatin; corticosteroids; non-steroidal anti-inflammatory drugs; anti-inflammatory compounds; anti-arrhythmic agents; antimicrobials; antibiotics; and the like.

In exemplary aspects, the steps of introducing the one or more additives into the reactor vessel can comprise opening the valve to allow the one or more additives to flow from the reservoir into the inlet port. Prior to pressurization, it is contemplated that the one or more additives can be introduced directly into the reactor vessel prior to sealing and/or via the inlet port.

It is contemplated that the disclosed rapid depressurization and repressurization of the reactor vessel, with or without the addition of the one or more additives, can be repeated for any desired number of cycles. It is further contemplated that the cycles of depressurization and repressurization, as well as the introduction of the primary sterilants and/or secondary sterilants and/or additives, can be automatically controlled via a controller that is configured to selectively open and/or close the various valves of the system to achieve desired pressure conditions and cycles.

In some aspects, the disclosed methods can further comprise the step of agitating the contents of the reactor vessel. In these aspects, it is contemplated that the step of agitating the contents of the reactor vessel can comprise periodically agitating the contents of the reactor vessel using a vibrator. It is further contemplated that the agitation of the reactor vessel can be intermittent, continual, or continuous. In exemplary aspects, the step of agitating the contents of the reactor vessel can occur during the step of introducing the primary sterilant into the reactor vessel. It is contemplated that the agitation of the contents of the reactor vessel can enhance the mass transfer of the sterilants and/or additives by eliminating voids in the fluids within the reactor vessel to provide for more complete contact between the ECM material and the sterilants and/or additives. It is further contemplated that the step of agitating the contents of the reactor vessel can comprise selectively adjusting the intensity and duration of agitation so as to optimize sterilization times, temperatures, and pressurization/depressurization cycles.

In a further aspect, after the sterilization and decellularization of the ECM material is complete, the method can further comprise depressurizing the reactor vessel and deactivating the magnetic drive so as to cease movement of the stirring impeller. Finally, the method can comprise the step of removing the resulting sterilized, acellular ECM composition through the top of the reactor vessel.

It is contemplated that the duration of the disclosed steps, as well as the temperatures and pressures associated with the disclosed steps, can be selectively varied to account for variations in the characteristics of the ECM material. For example, when the ECM material is a multi-laminate structure, has an increased thickness, or is positioned within a syringe, it is contemplated that the duration of the disclosed steps can be increased.

In one optional aspect, in order to make the sterilized, acellular ECM composition into a particulate form, the method can comprise cutting the ECM composition into pieces having desired lengths. In another aspect, the method can optionally comprise freeze-drying the pieces of the ECM composition. In an additional aspect, the method can optionally comprise grinding the frozen, hydrated pieces of the ECM composition and then passing the pieces of the ECM composition through a sizer screen until ECM particulate of a desired size is isolated. In a further optional aspect, the method can comprise rehydrating the ECM particulate with sterile saline or other sterile, biocompatible fluid to form an ECM suspension, as described herein.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Retrospective Evaluation of New Onset Postoperative Atrial Fibrillation in Patients Receiving the CorMatrix® ECM™

A retrospective, multi-center, two-arm, chart review was conducted in which the CorMatrix® ECM™ was utilized.

The objective of this retrospective trial was to assess whether utilization of the CorMatrix® ECM™ to reconstruct the normal pericardial barrier can result in a lower rate of new onset postoperative atrial fibrillation as compared to patients who did not undergo pericardial closure.

CorMatrix® ECM™ can be used for the reconstruction and repair of the pericardium following open heart surgery. Intact, the pericardium provides passive restraint to the heart preventing over dilation and helping to modulate abrupt volumetric changes. By reconstructing the pericardium with the CorMatrix® ECM™, the natural pericardial restraint can be restored. The purpose of this retrospective clinical trial was to assess if there is a reduction observed in new onset postoperative atrial fibrillation by analyzing patients who had their native pericardium reconstructed with the CorMatrix® ECM™ as compared to those who did not undergo pericardial closure following isolated coronary artery bypass graft (CABG) procedures.

The CorMatrix® ECM™ was supplied in four-ply sheets of various dimensions, which can be cut to size as the physician deems necessary for the procedure.

The definition of new onset postoperative atrial fibrillation used for this retrospective study is based on the definition used in the Society of Thoracic Surgeons (STS) Adult Cardiac Surgery Database 2007. The definition is as follows: "Indicate whether the patient had a new onset of Atrial Fibrillation/Flutter (AF) requiring treatment. Does not include recurrence of AF which had been present preoperatively. DO NOT include patients that had preoperative atrial fibrillation (treated or nontreated). The event must be of new origin.

All patients were required to meet the following inclusion criteria in order to be included as part of this retrospective clinical trial: this cardiac operation was the subject's first or primary cardiac operation, and the subject must have undergone an isolated CABG procedure.

Patients were not included as part of this retrospective clinical trial if one or more of the following exclusion criteria are met: prior history of atrial fibrillation, prior history of open heart surgery, prior history of pericarditis, prior history of amiodarone in the past six months, and concomitant valve surgery planned.

Patients who had their native pericardium reconstructed with the CorMatrix® ECM™ had a statistically significant decrease in the incidence of A-fib as compared to those who did not undergo pericardial closure following isolated CABG procedures. The usual incidence of A-fib is around 25%. For these studies, the A-fib incidence was between 4% and 8% (1/25 and 4/52).

Example 2

Modulation of Cardiac Remodeling with Acellular Matrix Emulsion is Associated with Myofibroblast Proliferation and Angiogenesis Via Recruiting C-Kit Positive Cells after Myocardial Infarction Degradation of native extracellular matrix (ECM) has been associated with maladaptive cardiac remodeling after infarction. As shown herein, xenogeneic acellular matrix emulsion injected into infarcted myocardium promoted myofibroblast proliferation and angiogenesis by recruiting host c-kit positive cells.

Sixty-four rats were subjected to 45 minutes regional ischemia followed by 3, 7, 21 and 42 days of reperfusion. Histological examination was performed by immunohistological staining, and cardiac function was analyzed using echocardiography. ECM emulsion (30-50 µl) was injected into the area at risk myocardium after reperfusion, and localization of the emulsion was confirmed with Masson Trichome staining. At 7 days of reperfusion, the population of c-kit positive cells within the emulsion area increased significantly relative to the control (32±0.6*vs. 15±3/1000 nuclei), consistent with significantly enhanced expression of 31 kDa stem cell factor detected by Western blotting. Along with this change, myofibroblasts accumulated in the emulsion region to a significant extent compared to the control (59±8*vs. 30±3/HPF). Strong immunoreactivity of VEGF was observed in the emulsion area and angiogenesis was significantly enhanced relative to the control, evidenced by increased density of a-smooth muscle actin-positive vessels (70±10*vs. 20±4/HPF) and vWF-positive vessels (95±14*vs. 34±8/HPF), respectively. At 42 days of reperfusion, echocardiography showed improvements in end-systolic volume (0.3±0.1*vs. 0.6±0.3 ml)), fractional shortening (33±5*vs. 24±6%) and ejection fraction (67±6*vs. 53±10%) in the emulsion group. The wall thickness of the infarcted middle anterior septum in the emulsion group was also significantly greater than that in the Control (0.19±0.02*vs. 0.15±0.02 cm).

Intramyocardial injection of an acellular extracellular matrix emulsion into the ischemic/reperfused myocardium attenuated maladaptive cardiac remodeling and preserved cardiac function, potentially mediated by enhanced myofibroblast proliferation and angiogenesis via recruiting c-kit positive cells. * $p<0.05$ emulsion vs. control.

Example 3

In exemplary applications of the disclosed sterilization and decellularization methods, selected tissues were harvested and rinsed in sterile saline. The selected tissues were then frozen for 24 hours. The frozen tissues were thawed in cold hypotonic tris buffer on ice with 5 mM ethylenediaminetetraacetic acid (EDTA). An extracellular matrix material was then isolated from each selected tissue, as described herein.

The isolated extracellular matrix materials were incubated for 24 to 48 hours in 0.5-1% Triton X-100/0.5-1% Deoxycholic acid with 5 mM EDTA in Dulbecco's Phosphate Buffered Saline (DPBS) (Lonza Walkersville, Inc.). Flat extracellular matrix materials, such as stomach submucosa (SS), small intestinal submucosa (SIS), and bladder submucosa (UBS), were incubated in a stretched configuration. Tubular extracellular matrix materials, such as ureters, arteries, veins, and tubular SIS, were perfused with the solutions through soaking and by use of a peristaltic pump.

After incubation, each extracellular matrix material was rinsed three times with DPBS. Each rinsing with DPBS lasted 30 minutes. Some extracellular matrix materials were then incubated for 2 to 12 hours at 37° C. in isotonic tris buffer containing 10-50 µg/mL of RNAse/0.2-0.5 µg/mL DNAse with 5 mM EDTA. Following this incubation step, the extracellular matrix materials were again rinsed three times with DPBS. Each rinsing with DPBS lasted 30 minutes. The extracellular matrix materials were stored at 4° C.

Within 48 hours of storage, the extracellular matrix materials were processed in supercritical carbon dioxide as disclosed herein for 20-60 minutes at temperatures at or greater than 31.1° C. and pressures at or greater than 1,071 psi. After this sterilization step, the extracellular matrix materials were rapidly depressurized at a rate of 2.7 MPa/10 sec. (391.6 psi/10 sec.) for a minute and 19 seconds. During this time, the pressure applied to the extracellular matrix materials rapidly decreased from 9.9 MPa to 0.69 MPa.

The extracellular matrix materials were then processed in supercritical carbon dioxide and peracetic acid (PAA) as disclosed herein for 30 minutes to 6 hours to achieve terminal sterilization. In this processing step, the pressure applied to the extracellular matrix materials was increased to 9.9 MPa. The resulting sterilized, acellular extracellular matrix materials were then packaged in Tyvek® (E.I. du Pont de Nemours & Company) pouches that were sealed within plastic pouches to prevent fluid leakage.

Table 1 summarizes the sterilization and decellularization of porcine ureter, bovine pericardium, and porcine mesothelium.

TABLE 1

| Material | Triton X-100 Conc. | Deoxycholic Acid Conc. | TX-100/ Deoxy incubation | RNAse/ DNAse incubation | Supercritical $CO_2$/PAA time |
|---|---|---|---|---|---|
| Porcine ureters | 0.5% | 0.5% | 24 hours | 2 hours | 120 minutes |
| Bovine pericardium | 0.5% | 0.5% | 24 hours | 2 hours | 180 minutes |
| Porcine mesothelium | 0.5% | 0.5% | 24 hours | 2 hours | 120 minutes |

Example 4

The DNA content of ECM material samples was measured as an indicator of decellularization of the respective ECM material samples using various sterilization and decellularization techniques. The measured DNA content was evaluated with a pico green assay in which DNA was labeled with a fluorescent label that was detected with a spectrophotometer. The measured DNA content was normalized by the dry weight of the samples. DNA content was measured and evaluated for the following treatment groups: (1) Lyophilized, non-sterile SIS; (2) Ethylene Oxide (EtO)-sterilized SIS; (3) Lyophilized, non-sterile SIS that was sterilized through a 60 minute treatment with PAA and supercritical $CO_2$, as disclosed herein; (4) Lyophilized, non-sterile SIS that was sterilized through a 20 minute treatment with PAA and supercritical $CO_2$, as disclosed herein; and (5) Raw, unprocessed SIS.

Figure 2:
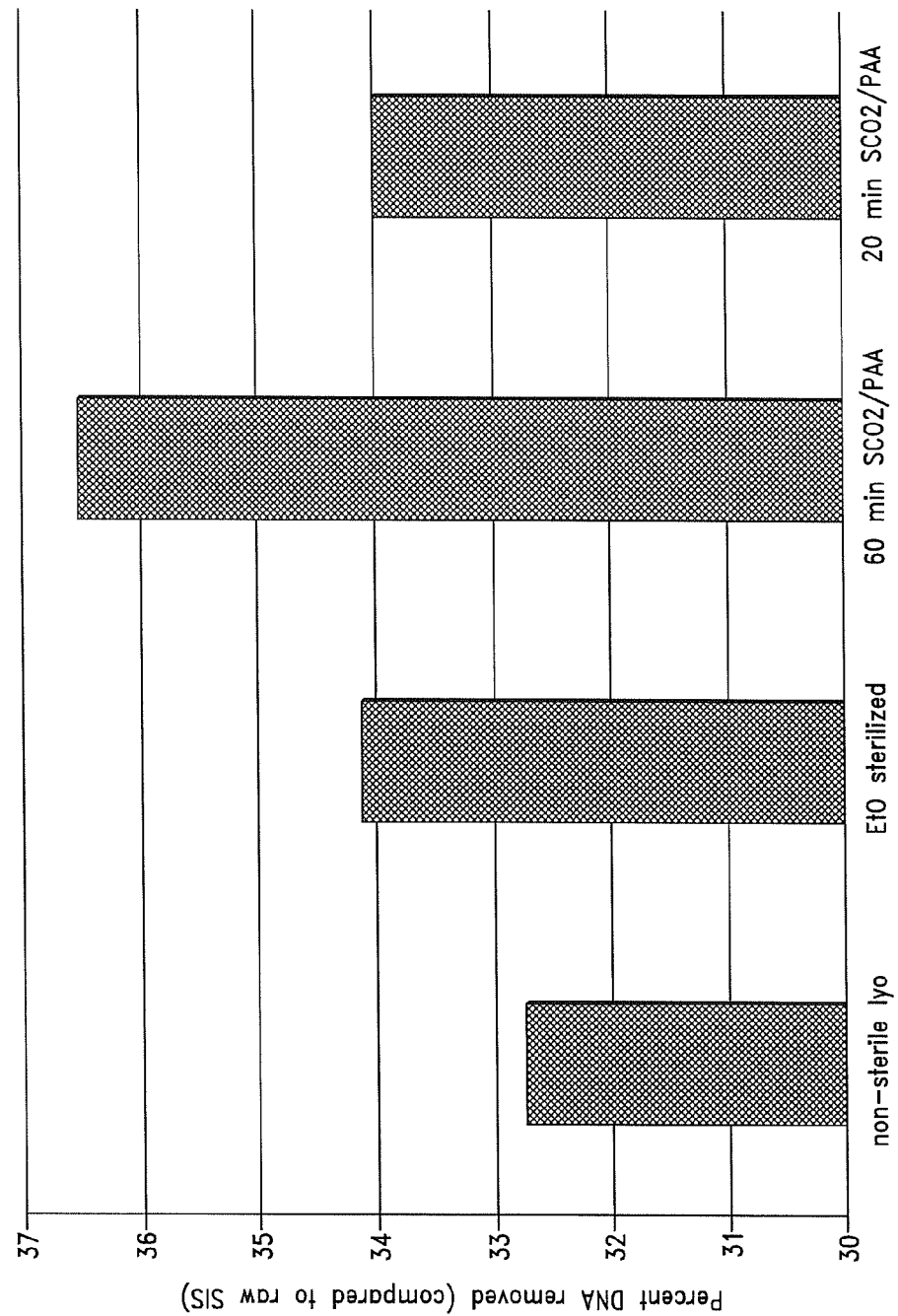

FIG. 1 shows the total DNA content for the respective samples, as normalized by dry weight. FIG. 2 shows the percent of DNA that was removed from each respective sample, as compared to raw, unprocessed SIS. These results indicated that by sterilizing the non-sterile SIS using a 60 minute treatment with PAA and supercritical $CO_2$, as disclosed herein, over 96% of the DNA found in raw SIS was removed, as compared to only 94% when the SIS was sterilized by EtO and only 93% when the SIS was not sterilized by any method.

Example 5

Ureters were processed with a gentle detergent (0.5% Triton X-100/0.5% Sodium Deoxycholate in 5 mM EDTA in DPBS) for 24 hours and then rinsed three times in DPBS as disclosed herein. After this pretreatment, the ureters were decellularized and sterilized using rapid depressurization and treatment with PAA and supercritical $CO_2$, as disclosed herein. Hematoxylin and Eosin (H&E) Stains were prepared for one sample ureter at the following stages of treatment: (A) native ureter; (B) pretreated ureter; and (C) pretreated ureter with rapid depressurization and treatment with PAA and supercritical $CO_2$, as disclosed herein. These stains indicated that DNA content was significantly reduced with rapid depressurization.

Example 6

Figure 3:
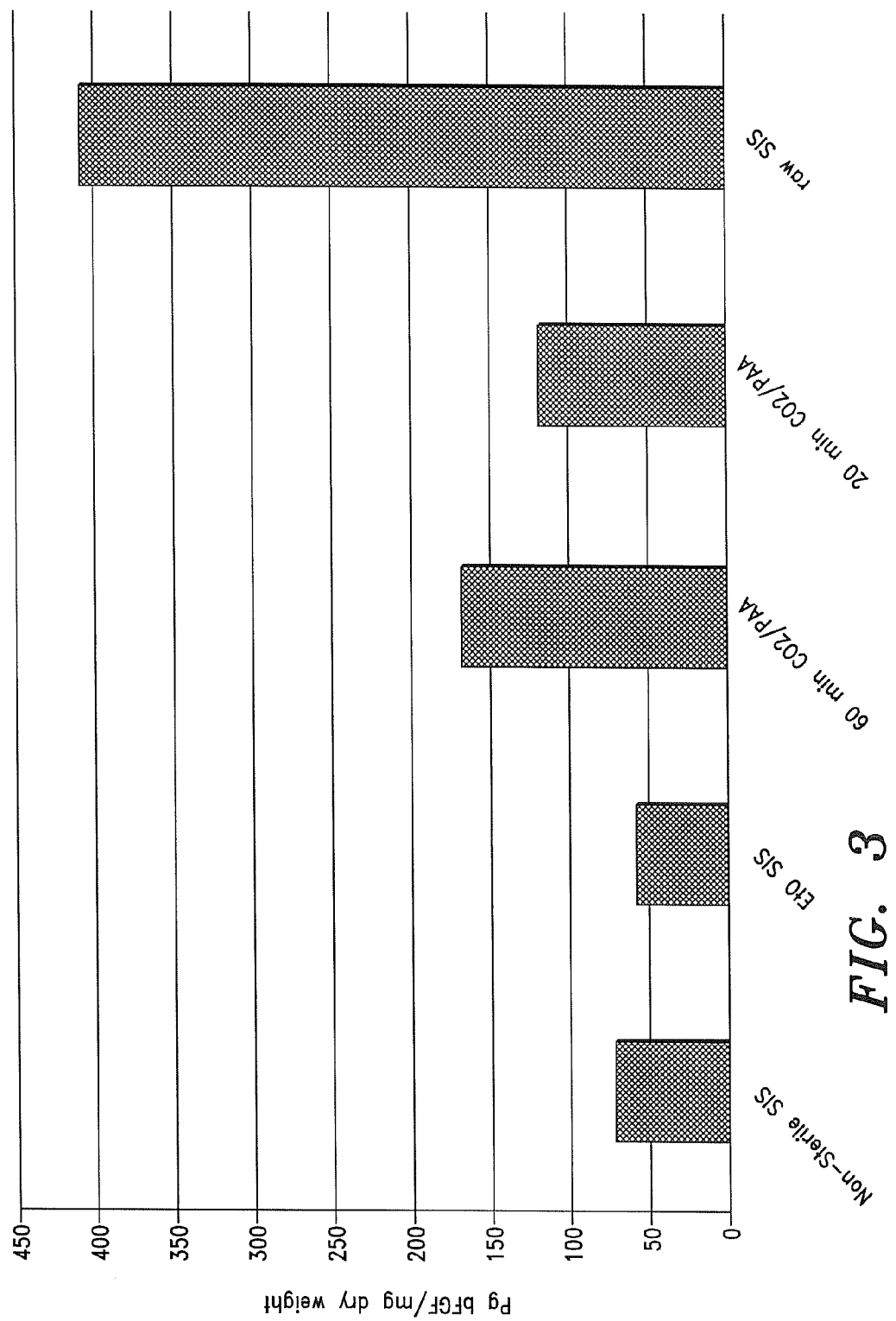
FIGS. 3-4 show the results of an experiment in which native growth factor content was measured for SIS compositions following various sterilization methods, including the sterilization methods described herein.
Figure 4:

The growth factor content of ECM material samples was measured. Enzyme-linked immunosorbent (ELISA) assays were performed on the ECM material samples to quantify the content of bFGF and the active form of TGF-13 in each respective sample. The following treatment groups were evaluated: (1) Lyophilized, non-sterile SIS; (2) Ethylene Oxide (EtO)-sterilized SIS; (3) Lyophilized, non-sterile SIS that was sterilized through a 60 minute treatment with PAA and supercritical $CO_2$, as disclosed herein; (4) Lyophilized, non-sterile SIS that was sterilized through a 20 minute treatment with PAA and supercritical $CO_2$, as disclosed herein; and (5) Raw, unprocessed SIS. The bFGF content and TGF-$\beta$ content measurements were normalized by dry weight of each respective sample. These results are shown in FIGS. 3 and 4. These results indicated that the concentration of both growth factors was reduced by exposure to EtO. However, the concentration of the growth factors was not affected by sterilization with PAA and supercritical $CO_2$.

Example 7

Figure 5:
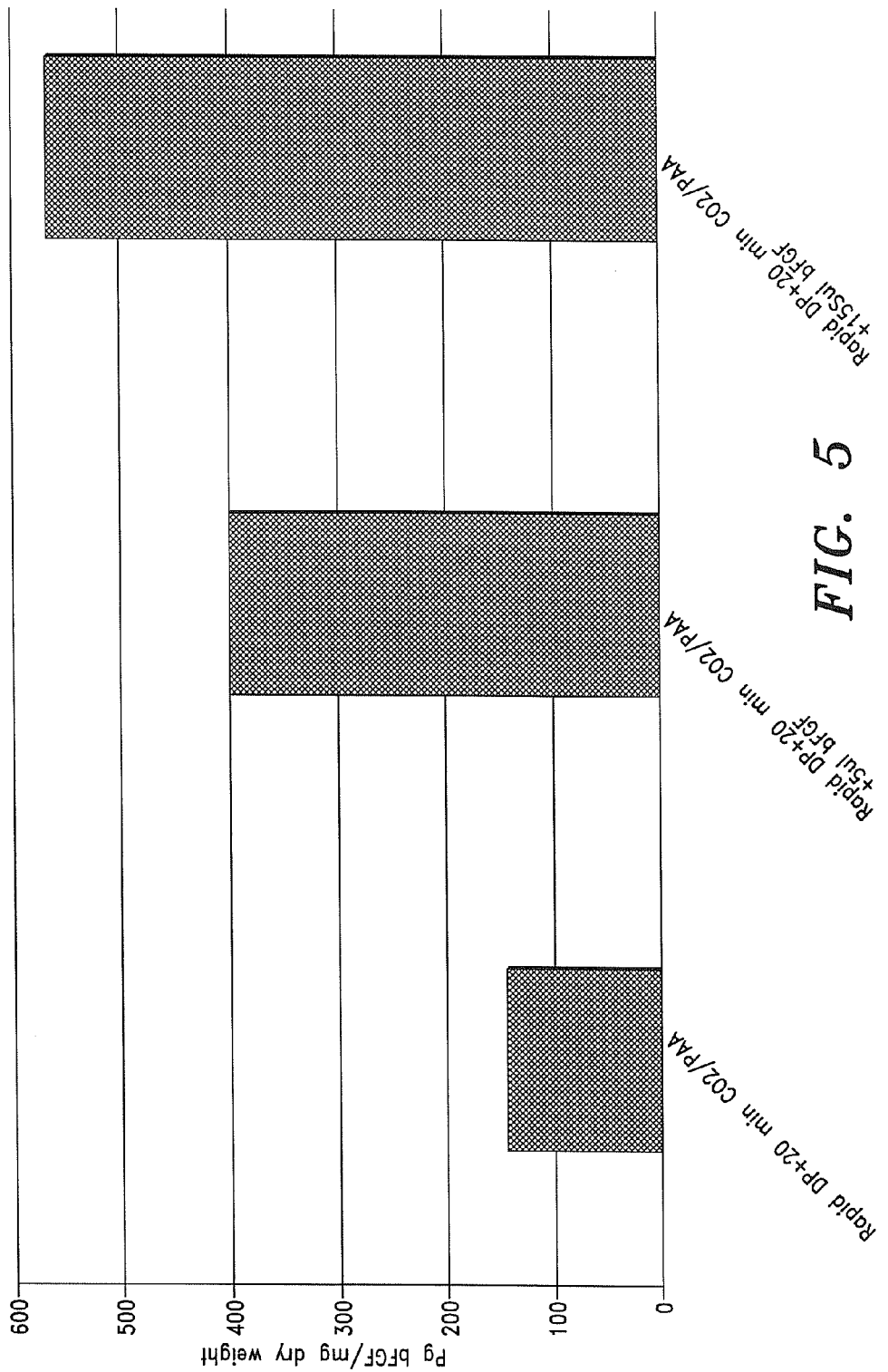
FIG. 5 shows the results of an experiment in which bFGF was incorporated into SIS compositions during rapid depressurization, as described herein.

Using the methods disclosed herein, supercritical $CO_2$ was used as a primary sterilant and as a carrier for adding bFGF into SIS sheets. First, the respective SIS sheets were placed into Tyvek® pouches along with varying amounts of bFGF. The pouches were exposed to supercritical $CO_2$ for 60 minutes at 9.6 MPa. The pouches were rapidly depressurized at a rate of 7.20 MPa/min. Samples were directly processed in 16 mL PAA in supercritical $CO_2$ for 20 minutes. The following treatment groups were evaluated: (1) No bFGF added; (2) 5 μL bFGF added; and (3) 15 μL bFGF added. Each 4 of bFGF contained 0.1 μg of bFGF. Thus, since each SIS sheet weighed approximately 0.5 g, the maximum concentrations of bFGF for the 5 μL and 15 μL groups were about 4170 pg/mg dry weight and about 12,500 pg/mg dry weight, respectively. The bFGF content for these groups is shown in FIG. 5, as measured with respect to the dry weight of the respective samples. These results indicated that the measured concentrations of bFGF did not reach the maximum concentrations and that the sample to which 15 μL of bFGF was added did not have a measured concentration of bFGF that was three times greater than the measured concentration of bFGF in the sample to which 5 μL of bFGF was added.

Example 8

Figure 6:
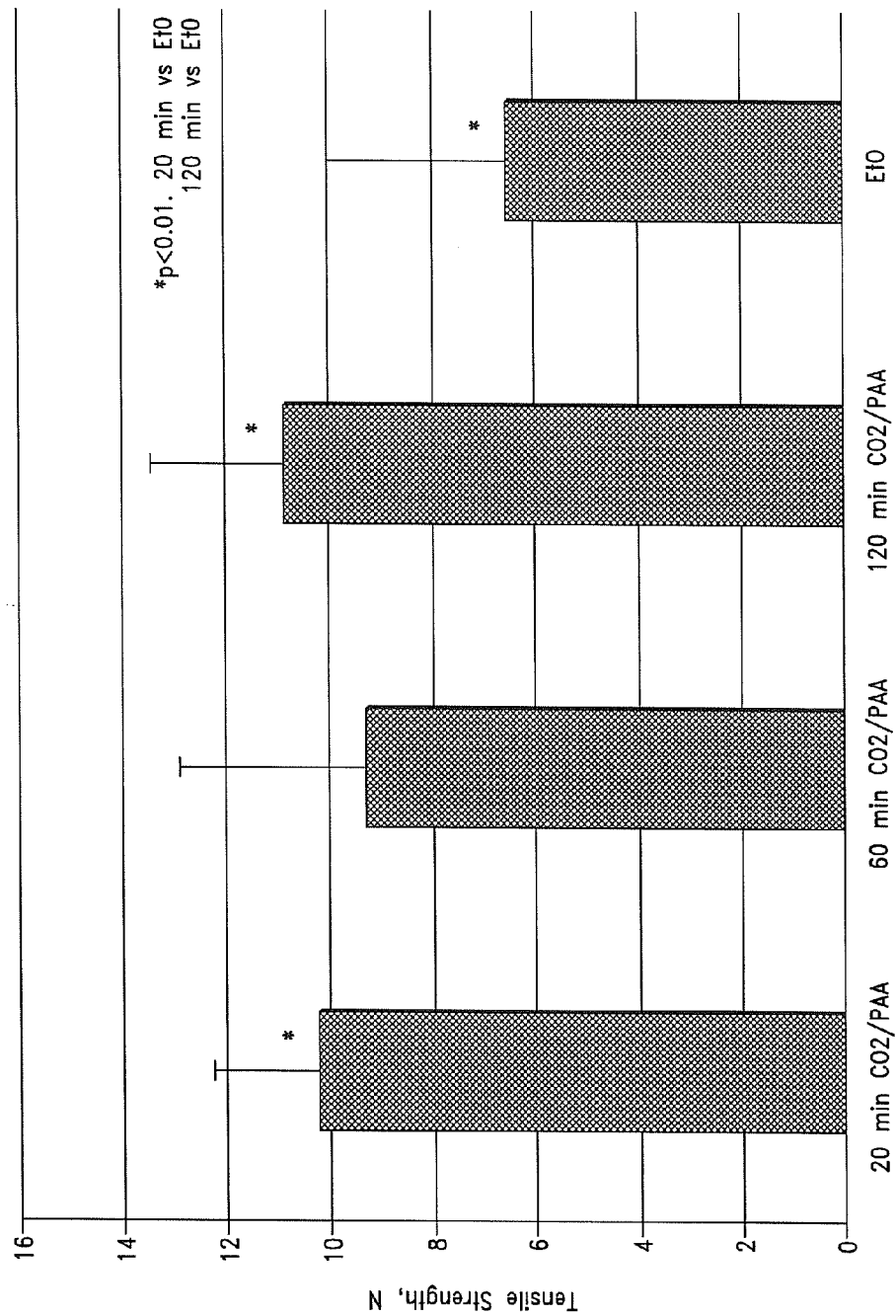
FIG. 6 shows the results of an experiment in which the tensile strength of two-ply SIS compositions was measured following various sterilization methods, including the sterilization methods described herein.

The tensile strengths of two-ply SIS samples were measured. The following treatment groups were evaluated: (1) EtO Treatment; (2) PAA/supercritical $CO_2$ treatment for 20 minutes; (3) PAA/supercritical $CO_2$ treatment for 60 minutes; and (4) PAA/supercritical $CO_2$ treatment for 120 minutes. The tensile strength test results are shown in FIG. 6. These results indicated that the SIS samples that were processed with PAA/supercritical $CO_2$ for 20 or 120 minutes, as disclosed herein, were significantly stronger than the SIS samples that were processed with EtO.

Example 9

Rapid depressurization was used following gentle detergent soaks or perfusion of the ECM materials listed in Table 2 (below) at the noted concentrations and for the noted time periods. Tissues were harvested and rinsed in saline. The tissues were frozen for at least 24 hours. The tissues were thawed in cold hypotonic tris buffer on ice with 5 mM EDTA. The ECM of interest was isolated. For flat tissues (e.g., stomach submucosa, small intestine submucosa, and bladder submucosa), the tissue was stretched on a tissue stretching device and incubated in solutions in a stretched configuration. For tubular tissues (e.g., ureters, arteries, veins, and tubular SIS), the tissue was perfused with solutions using a peristaltic pump and were soaked during incubation. The tissues were incubated for 2 to 24 hours in 0.5% Triton X-100/0.5% Deoxycholic acid with 5 mM EDTA in DPBS. The tissues were rinsed 3 times for 15-30 minutes each time in DPBS. The tissues were stored at 4° C. Within 48 hours of tissue storage, the tissues were processed in supercritical $CO_2$ for 20-120 minutes followed by rapid depressurization (RDP) (decrease in pressure from 9.9 MPa to 0.69 MPa in 1 min 19 sec, corresponding to a depressurization of 2.7 MPa/10 sec).

TABLE 2

| Material | Triton X-100 Conc. | Deoxycholic Acid Conc. | TX-100/Deoxy incubation | Supercritical $CO_2$ time |
|---|---|---|---|---|
| Porcine ureters | 0.5% | 0.5% | 24 hours | 60 minutes |
| Bovine pericardium | 0.5% | 0.5% | 24 hours | 60 minutes |
| Porcine mesothelium | 0.5% | 0.5% | 2 hours | 60 minutes |
| SIS | 0.5% | 0.5% | 2 hours | 60 minutes |

The results showed that supercritical $CO_2$ exposure followed by rapid depressurization ($SCCO_2$+RDP) did aid in the removal of cell remnants and DNA while preserving growth factors in the ECMs.

Example 10

The growth factor content of various ECM compositions was analyzed using basic fibroblast growth factor (bFGF) as a representative growth factor. bFGF was selected because it is a prevalent growth factor in native ECM tissues. An enzyme-linked immunosorbent assay (ELISA, R&D Systems, Minneapolis, Minn.) was used to measure the bFGF content in the following samples: (1) Unprocessed (Raw) SIS; (2) SIS after detergent soak (TX-deoxy) only; (3) SIS after TX-deoxy and RDP (includes $SCCO_2$); (4) SIS after TX-deoxy, RDP, and PAA ($SCCO_2$ with PAA for sterilization); (5) SIS after TX-deoxy, and PAA; (6) SIS sterilized by EtO (supplied by Cook Biotech, Inc.); and (7) non-sterile SIS (supplied by Cook Biotech, Inc.).

Figure 7:
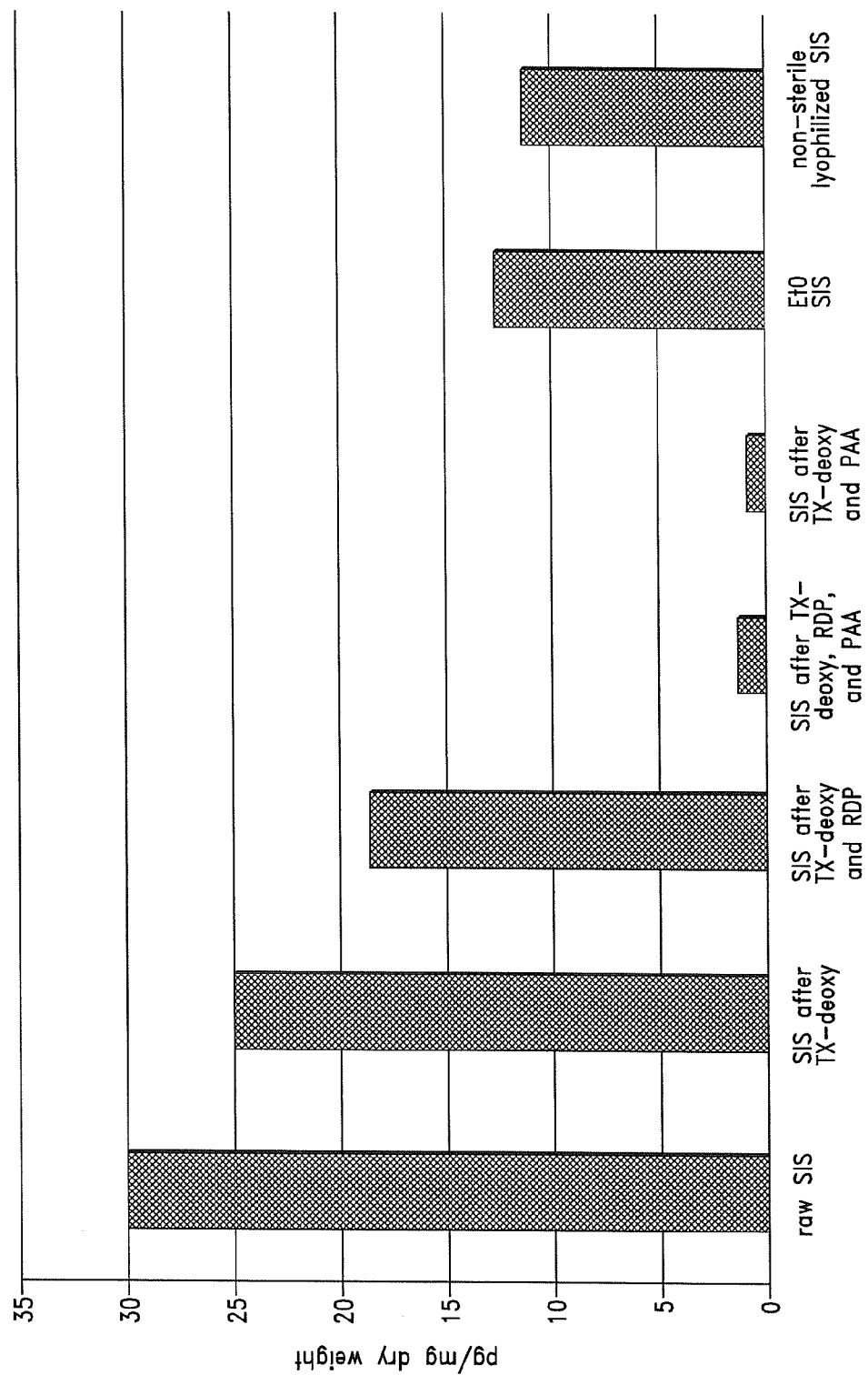
FIG. 7 shows the results of an experiment in which native growth factor content was measured for SIS compositions following various sterilization and/or decellularization methods, including the sterilization and decellularization methods described herein.
Figure 8:
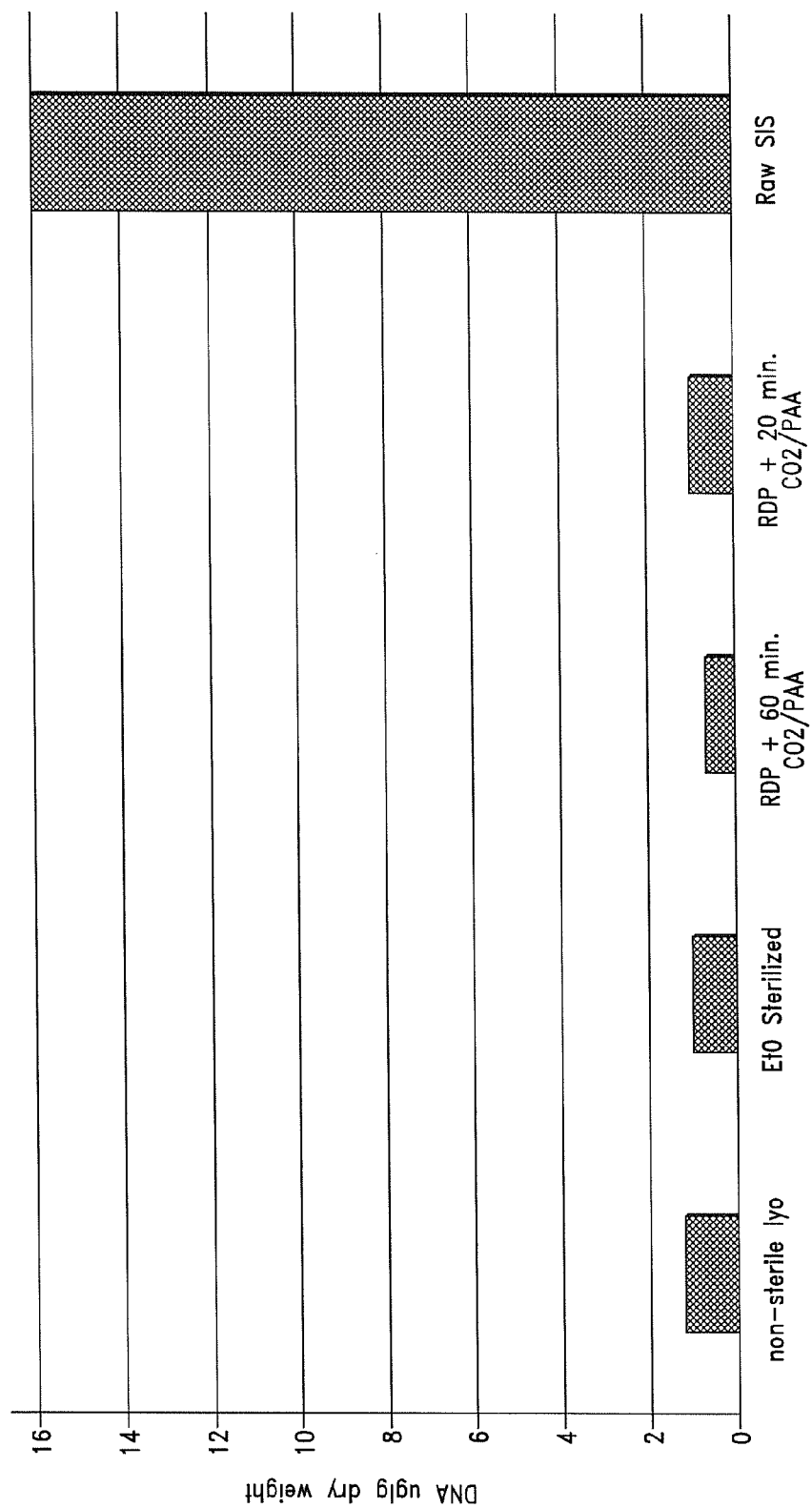
FIG. 8 shows the DNA content in SIS after it is processed in various ways. The baseline measurement is raw. The tissue was then exposed to supercritical $CO_2$ followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 9:
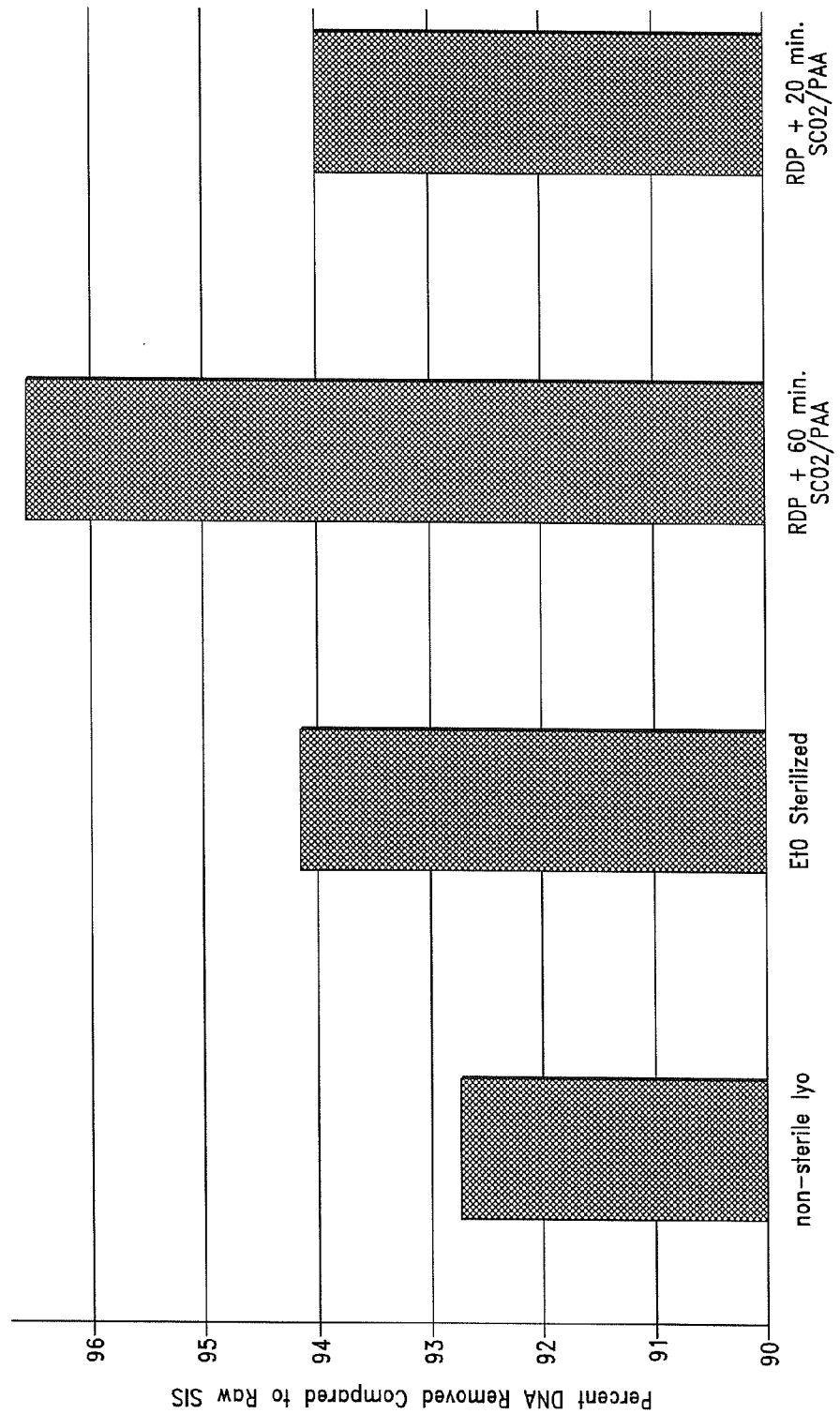
FIG. 9 shows the Percent removal of DNA from SIS after it is processed in various ways. The baseline measurement is raw. The tissue was then exposed to supercritical $CO_2$ followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 10:
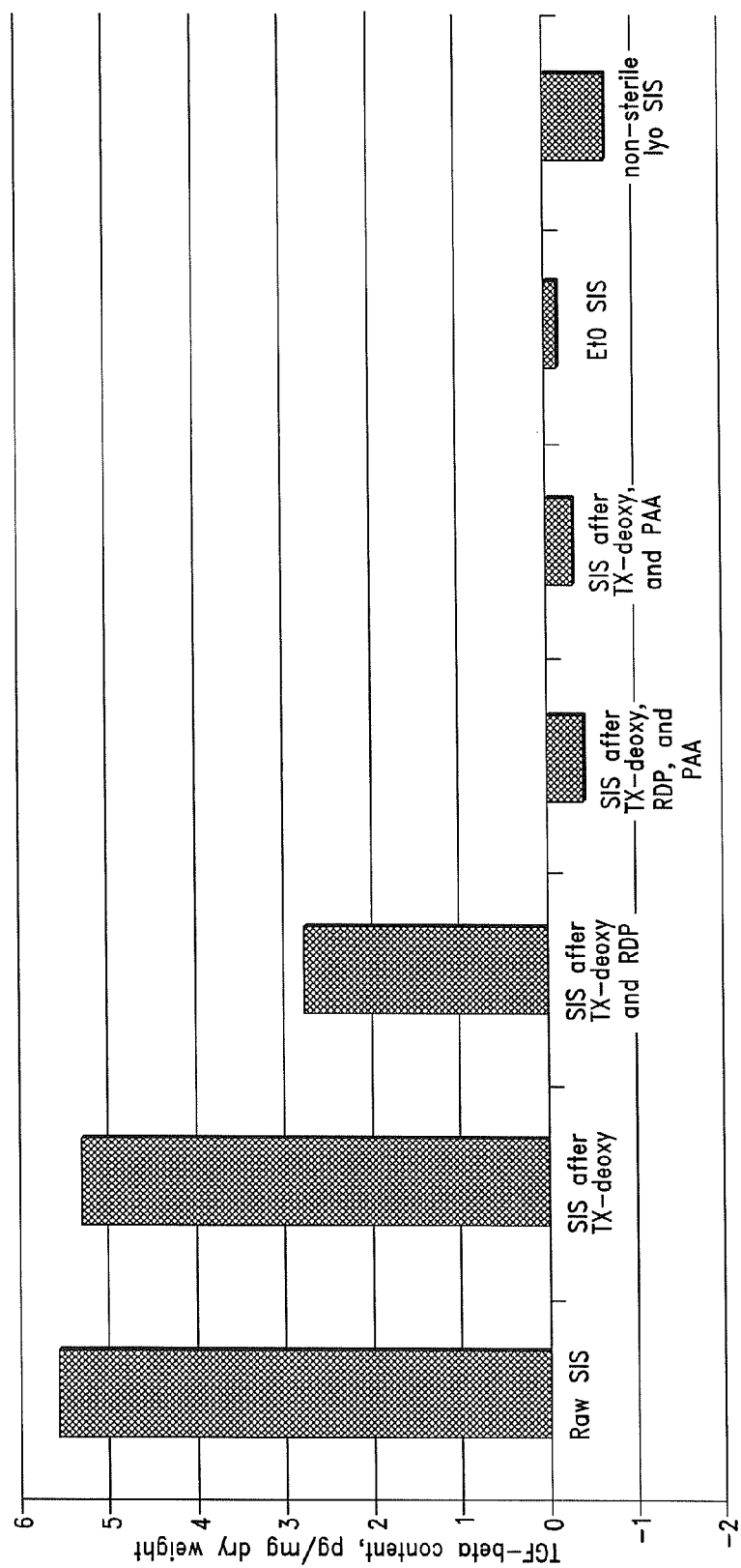
FIG. 10 shows the variable active Transforming Growth Factor (TGF-beta) content in SIS after it is processed in various ways. The baseline measurement is raw, or unprocessed SIS followed by processing with only Triton X-100 (TX-100) detergent. The tissue was then exposed to supercritical $CO_2$ followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 11:
FIG. 11 shows the variable basic Fibroblast Growth Factor (bFGF) content in SIS after it is processed in various ways. The baseline measurement is raw, or unprocessed SIS followed by processing with only Triton X-100 (TX-100) detergent. The tissue was then exposed to supercritical $CO_2$ followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 12:
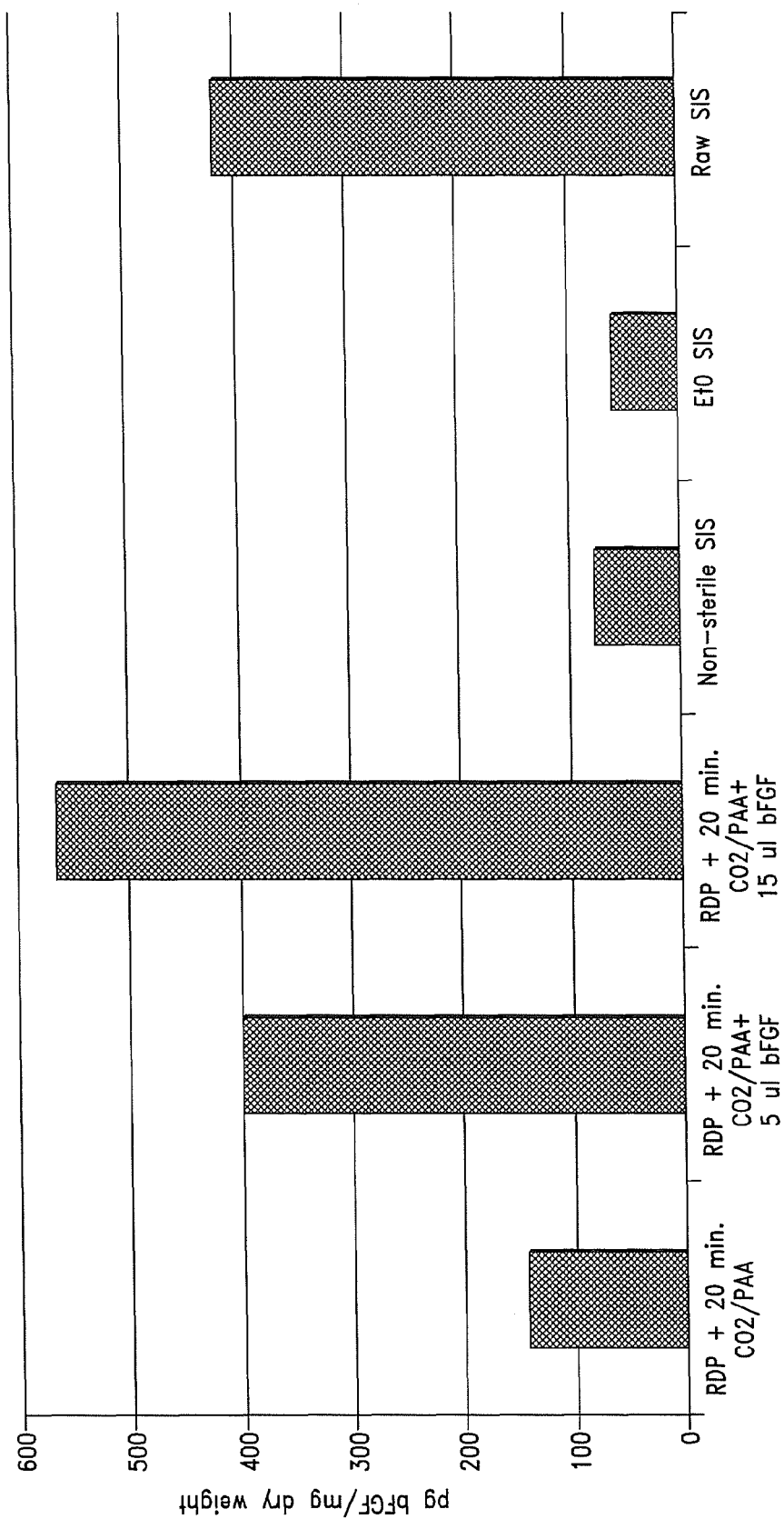
FIG. 12 shows the addition of basic Fibroblast Growth Factor (bFGF) content to SIS using rapid depressurization. The baseline measurement is raw, or unprocessed SIS. The comparison is to processed SIS either unsterilized or sterilized with ethylene oxide (ETO).

In these studies, SIS was used to compare an ECM composition processed with and without RDP to SIS provided by Cook Biotech, Inc. Some of the processed SIS was also sterilized using the described $SCCO_2$+PAA method after decellularization. The measured growth factor content of the respective ECM compositions is shown in FIG. 7.

These results indicate that the rapid depressurization process was more effective than other decellularization processes at preserving the bFGF content and that the additional RDP processing to remove residual DNA and cell fragments results in only a small loss of bFGF. By comparison, the PAA sterilization process appeared to remove almost all of the remaining bFGF, even in the absence of RDP. Additionally, the rapid depressurization process preserved more of the bFGF content in the native SIS than the Cook decellularization methods. For purposes of these results, when the bFGF content was reduced, it is assumed that all other growth factor content was similarly reduced since the growth factors are all bound to the ECM compositions in a similar manner.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An extracellular matrix (ECM) composition for treating post-operative atrial fibrillation, comprising:
    an ECM scaffold comprising sterilized, acellular mesothelial tissue, said mesothelial tissue comprising a pre-processing dry weight transforming growth factor beta (TGF-β) content of at least 5.5 pg/mg and a pre-processing dry weight basic fibroblast growth factor (bFGF) content of at least 30 pg/mg,
    said mesothelial tissue being contemporaneously sterilized and decellularized by introducing said mesothelial tissue into a reactor pressure vessel, introducing at least a first sterilant comprising carbon dioxide ($CO_2$) into said reactor pressure vessel at a first controlled pressurization rate, pressurizing said reactor pressure vessel at a pressure in the range of approximately 1000-3500 psi and at a temperature in the range of 25°-60° C., maintaining said mesothelial tissue in contact with said first sterilant for a minimum first processing time no less than 10 min. and depressurizing said reactor pressure vessel at a first depressurizing rate, said first depressurizing rate being in the range of 725-1450 psi/min,
    wherein said steps of introducing said $CO_2$ into said vessel interior space and maintaining said vessel pressure and temperature are performed at a maximum second processing time no greater than 60 minutes, and
    wherein said mesothelial tissue is rendered at least 96% acellular,
    said mesothelial tissue further comprising a post-processing dry weight TGF-β content of at least 2.8 pg/mg, and a post-processing dry weight bFGF content of at least 19 pg/mg, and
    wherein, when said ECM scaffold is administered to damaged myocardial tissue of a subject, said ECM scaffold modulates inflammation of said damaged myocardial tissue induces myofibroblast proliferation and angiogenesis and, thereby, bioremodeling and regeneration of new myocardium tissue, whereby said ECM scaffold modulates electrical activity of said subject's heart.

2. The ECM composition of claim 1, further comprising introducing a second sterilant into said interior space of said reactor vessel with said carbon dioxide, said second sterilant comprising trifluoroacetic acid.

3. A sterilized, acellular extracellular matrix (ECM) composition for treating post-operative atrial fibrillation, comprising:
    an ECM scaffold comprising sterilized, acellular mesothelial tissue, comprising a pre-processing dry weight transforming growth factor beta (TGF-β) content of at least 5.5 pg/mg and a pre-processing dry weight basic fibroblast growth factor (bFGF) content of at least 30 pg/mg, said mesothelial tissue being contemporaneously sterilized and decellularized by introducing said mesothelial tissue into a reactor pressure vessel, introducing at least a first sterilant comprising carbon dioxide ($CO_2$) into said reactor pressure vessel at a first controlled pressurization rate, pressurizing said reactor pressure vessel at a pressure in the range of approximately 1000-3500 psi and at a temperature in the range of 25°-60° C., maintaining said mesothelial tissue in contact with said first sterilant for a minimum first processing time no less than 10 min. and depressurizing said reactor pressure vessel at a first depressurizing rate, said first depressurizing rate being in the range of 725-1450 psi/min, introducing at least a first additive into said interior space of said reactor vessel during said rapid depressurization step, wherein said steps of introducing said $CO_2$ into said vessel interior space and maintaining said vessel pressure and temperature are performed at a maximum second processing time no greater than 60 minutes, and wherein said mesothelial tissue is rendered at least 96% acellular, said mesothelial tissue further comprising a post-processing dry weight TGF-β content of at least 2.8 pg/mg, a post-processing dry weight bFGF content of at least 19 pg/mg and said first additive, and wherein, when said ECM scaffold is administered to damaged myocardial tissue of a subject, said ECM scaffold modulates inflammation of said damaged myocardial tissue induces myofibroblast proliferation and angiogenesis and, thereby, bioremodeling and regeneration of new myocardium tissue, whereby said ECM scaffold modulates electrical activity of said subject's heart.

4. The ECM composition of claim 3, further comprising introducing a second sterilant into said interior space of said reactor vessel with said carbon dioxide, said second sterilant comprising trifluoroacetic acid.

5. The ECM composition of claim 3, wherein said first additive comprises a statin selected from the group consisting of lovastatin, simvastatin, atorvastatin, fluvastatin, pravastatin, rosuvastatin, cerivastatin and pitavastatin.

6. The ECM composition of claim 3, wherein said first additive comprises an anti-arrhythmic agent selected from the group consisting of quinidine, procainamide, disopyramide, lidocaine, phenyloin, mexiletine, flecamide, propafenone, moricizine, propranolol, esmolol, timolol, metoprolol, atenolol, amiodarone, sotalol, ibutilide, dofetilide, verapamil, diltiazem, adenosine and digoxin.

7. The ECM composition of claim 3, wherein said first additive comprises an antibiotic.

8. The ECM composition of claim 3, wherein said cardiac arrhythmia comprises atrial fibrillation.

\* \* \* \* \*